(12) United States Patent
Ebner et al.

(10) Patent No.: US 7,737,257 B2
(45) Date of Patent: Jun. 15, 2010

(54) CONNECTIVE TISSUE GROWTH FACTOR (CTGF-3)

(75) Inventors: Reinhard Ebner, Gaithersburg, MD (US); Arvind Chopra, Gaithersburg, MD (US); Steven M. Ruben, Brookeville, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 42 days.

(21) Appl. No.: 11/962,282

(22) Filed: Dec. 21, 2007

(65) Prior Publication Data

US 2009/0074778 A1 Mar. 19, 2009

Related U.S. Application Data

(63) Continuation of application No. 10/721,336, filed on Nov. 26, 2003, now abandoned, which is a continuation of application No. 09/712,142, filed on Nov. 15, 2000, now abandoned, which is a continuation of application No. 08/966,020, filed on Nov. 7, 1997, now abandoned.

(60) Provisional application No. 60/030,720, filed on Nov. 8, 1996.

(51) Int. Cl.
| | |
|---|---|
| C07K 16/18 | (2006.01) |
| C07K 16/46 | (2006.01) |
| C07K 16/22 | (2006.01) |
| C07K 16/24 | (2006.01) |
| C07K 16/26 | (2006.01) |
| C12N 5/00 | (2006.01) |
| G01N 33/53 | (2006.01) |

(52) U.S. Cl. .............. 530/387.1; 530/387.3; 530/388.1; 530/389.1; 530/389.2; 530/391.3; 530/866; 435/7.1; 435/326

(58) Field of Classification Search ........................ None
See application file for complete search history.

(56) References Cited

U.S. PATENT DOCUMENTS

| 5,408,040 A | 4/1995 | Grotendorst et al. |
| 6,387,657 B1 | 5/2002 | Botstein et al. |

FOREIGN PATENT DOCUMENTS

| EP | 0 495 674 A2 | 7/1992 |
| WO | WO-93/00430 | 1/1993 |
| WO | WO-96/01896 | 1/1996 |
| WO | WO-96/38168 | 12/1996 |
| WO | WO-98/58063 | 12/1998 |
| WO | WO-99/14327 | 3/1999 |
| WO | WO-99/21998 | 5/1999 |

OTHER PUBLICATIONS

Alberts, et al., *Molecular Biology of the Cell*, Garland Publishing, Inc., New York, NY, pp. 1181-1187 (Jan. 1994).

Barton, G.J., "Protein sequence alignment and database scanning," in *Protein Structure Predication, A Practical Approach*, IRL Press at Oxford University Press, Oxford, UK, pp. 31-63 (1996).
Benjamini, et al., "Antigenicity," in: *Immunology, A Short Course*, Wiley-Liss, New York, NY, pp. 40 (1991).
Bork, P., "The modular architecture of a new family of growth regulators related to connective tissue growth factor," *FEBS Lett.*, 327:125-130 (1993).
Bowie, et al., "Deciphering the message in protein sequences: tolerance to amino acid substitutions," *Science*, 247:1306-1310 (1990).
Bradham, et al., "Connective tissue growth factor: a cysteine-rich mitogen secreted by human vascular endothelial cells is related to the SRC-induced immediate early gene product CEF-10," *J. Cell Biol.*, 114(6):1285-1294 (1991).
Brigstock, D.R., "The connective tissue growth factor/cysteine-rich 61/nephroblastoma overexpressed (CCN) family," *Endocr. Rev.*, 20:189-206 (Apr. 1999).
Daniel, et al., "Mapping of linear antigenic sites on the S glycoprotein of a neurotropic murine coronavirus with synthetic peptides: a combination of nine prediction algorithms fails to identify relevant epitopes and peptide immunogenicity is drastically influenced by the nature of the protein carrier," *Virol.*, 202(2):540-549 (Aug. 1, 1994).
DiCorleto, P.E., "Cultured endothelial cells produce multiple growth factors for connective tissue cells," *Exp. Cell Res.*, 153:167-172 (1984).
George, et al., "Current methods in sequence comparison and analysis," in: *Macromolecular Sequencing and Sysnthesis, Selected Methods and Applications*, D.H. Schlesinger (ed.), Alan R. Liss, Inc., New York, NY, pp. 127-149 (1988).
Grotendorst, et al., "Individual domains of connective tissue growth factor regulate fibroblast proliferation and myofibroblast differentiation," *The FASEB Journal*, 19:729-738 (May 2005).
Grotendorst, G.R., "Connective tissue growth factor: a mediator of TGF-β action on fibroblasts," *Cytokine & Growth Factor Reviews*, 8:171-179 (Sep. 1997).
Henikoff, et al., "Gene families: the taxonomy of protein paralogs and chimeras," *Science*, 278:609-614 (Oct. 1997).
Igarash, et al., "Connective tissue growth factor," *J. Dermatol.*, 19:642-643 (1992).
Igarashi, et al., "Significant correlation between connective tissue growth factor gene expression and skin sclerosis in tissue sections from patients with systemic sclerosis," *J. Invest. Dermatol.*, 105:280-284 (Aug. 1995).
Igarashi, et al., "Connective tissue growth factor gene expression in tissue sections from localized scleroderma keloid, and other fibrotic skin disorders," *J. Invest. Dermatol.*, 106:729-733 (Apr. 1996).
Inadera, et al., "WISP-2 as a novel estrogen-responsive gene in human breast cancer cells," *Biochem. Biophys. Res. Commun.*, 275:108-114 (Aug. 2000).
Inadera, et al., "WISP-2 is a secreted protein and can be a marker of estrogen exposure in MCF-7 cells," *Biochem. Biophys. Res. Commun.*, 294:602-608 (Jun. 2002).

(Continued)

*Primary Examiner*—David S Romeo

(57) ABSTRACT

The present invention relates to a novel connective tissue growth factor-3 protein which is a member of the growth factor superfamily. In particular, isolated nucleic acid molecules are provided encoding the human connective tissue growth factor-3 protein. Connective tissue growth factor-3 polypeptides are also provided as are vectors, host cells and recombinant methods for producing the same. Also provided are diagnostic and therapeutic methods for detecting and treating connective tissue related disorders.

20 Claims, 4 Drawing Sheets

OTHER PUBLICATIONS

Jalkanen, et al., "Heparan sulfate proteoglycans from mouse mammary epithelial cells: localization on the cell surface with a monoclonal antibody," *J. Cell Biol.*, 101:976-984 (1985).

Jalkanen, et al., "Cell surface proteoglycans of mouse mammary epithelial cells is shed by cleavage of its matrix-binding ectodomain from its membrane-associated domain," *J. Cell Biol.*, 105(6, Pt. 2):3087-3096 (1987).

Kumar, et al., "Identification and cloning of a connective tissue growth factor-like cDNA from human osteoblasts encoding a novel regulator of osteoblast functions," *J. Biol. Chem.*, 274:17123-17131 (Jun. 1999).

Leask, et al., "All in the CCN family: essential matricellular signaling modulators emerge from the bunker," *Journal of Cell Science*, 119:4803-4810 (2006).

Luckow, et al., "High level expression of nonfused foreign genes with *Autographa californica* nuclear polyhedrosis virus expression vectors," *Virol.*, 170:31-39 (1989).

Mason, et al., "The growth arrest-specific gene CCN5 is deficient in human leiomyomas and inhibits the proliferation and motility of cultured human uterine smooth muscle cells," *Molecular Human Reproduction*, 10(3):181-187 (Mar. 2004).

Mathews, et al., *Biochemistry, Second Edition*, The Benjamin/Cummings Publishing Company, Inc., Menlo Park, CA, pp. 142-146 (1996).

NCBI Entrez, GenBank Accession No. C01967, Okubo, K. (Jul. 1996).

NCBI Entrez, GenBank Accession No. AA187512, Hillier, L., et al. (Jan. 1997).

NCBI Entrez, GenBank Accession No. AA304688, Adams, M.D., et al. (Apr. 1997).

NCBI Entrez, GenBank Accession No. AA318364, Adams, M.D., et al. (Apr. 1997).

NCBI Entrez, GenBank Accession No. AA373233, Adams, M.D., et al. (Apr. 1997).

NCBI Entrez, GenBank Accession No. AA373257, Adams, M.D., et al. (Apr. 1997).

NCBI Entrez, GenBank Accession No. AA373788, Adams, M.D., et al. (Apr. 1997).

NCBI Entrez, GenBank Accession No. AA374371, Adams, M.D., et al. (Apr. 1997).

NCBI Entrez, GenBank Accession No. AA374626, Adams, M.D., et al. (Apr. 1997).

NCBI Entrez, GenBank Accession No. AA377456, Adams, M.D., et al. (Apr. 1997).

NCBI Entrez, GenBank Accession No. AA385680, Adams, M.D., et al. (Apr. 1997).

NCBI Entrez, GenBank Accession No. AA717584, Marra, M., et al. (Dec. 1997).

NCBI Entrez, GenBank Accession No. AA754979, Marra, M., et al. (Jan. 1998).

NCBI Entrez, GenBank Accession No. AA187512, Hillier, L., et al. (1997).

Ngo, et al., in *The Protein Folding Problem and Tertiary Structure Prediction*, Merz and Le Grand (eds), Springer Verlag, pp. 433 and 492-495 (Aug. 1994).

Oemar, et al., "Human connective tissue growth in atherosclerosis and restenosis," *Circulation (Suppl. 1)*, 92(8):1-170 (Abstract 0811) (Oct. 1995).

Pennica, et al., "*WISP* genes are members of the connective tissue growth factor family that are up-regulated in Wnt-1 transformed cells and aberrantly expressed in human colon tumors," *Proc. Natl. Acad. Sci. USA*, 95:14717-14722 (Dec. 1998).

Ryseck, et al., "Structure, mapping, and expression of *fisp-12*, a growth factor-inducible gene encoding a secreted cysteine-rich protein," *Cell Growth & Differentiation*, 2:225-233 (1991).

Sambrook, et al., "Analysis and cloning of eukaryotic genomic DNA," in: *Molecular Cloning: A Laboratory Manual Second Edition*, Cold Spring Harbor Laboratory Press, Cold Spring Harbor, NY, vols. 1, 2 and 3, pp. 9-50 (1989).

Sambrook, et al., "Expression of cloned genes in cultured mammalian cells," Chapter 16 and Chapter 17, p. 17.2 in: *Molecular Cloning: A Laboratory Manual, Second Edition*, Cold Spring Harbor Laboratory Press, Cold Spring Harbor, New York, U.S.A. (1989).

Saxena, et al., "Differential expression of WISP-1 and WISP-2 genes in normal and transformed human breast cell lines," *Mol. Cell. Biochem.*, 228:99-104 (Dec. 2001).

Smith, et al., "Single-step purification of polypeptides expressed in *Escherichia coli* as fusions with glutathione S-transferase," *Gene*, 67:31-40 (1988).

Smith, et al., "Comparison of biosequences," *Adv. in Appl. Math.*, 2:482-489 (1981).

Xin, et al., "Differential expression of novH and CTGF in human glioma cell lines," *J. Clin. Pathol.: Mol. Pathol.*, 49:M91-M97 (Apr. 1996).

Zhang, et al., "Identification of rCop-1, a new member of the CCN protein family, as a negative regulator for cell transformation," *Mol Cell Biol.*, 18(10):6131-6141 (Oct. 1998).

Zoubine, et al., "WISP-2: a serum-inducible gene differentially expressed in human normal breast epithelial cells and in MCF-7 breast tumor cells," *Biochem. Biophys. Res. Commun.*, 282:421-425 (Mar. 2001).

```
               10                      30                      50
                .                       .                       .
     CAGGGGACATGAGAGGCACACCGAAGACCCACCTCCTGGCCTTCTCCCTCCTCTGCCTCC
              MetArgGlyThrProLysThrHisLeuLeuAlaPheSerLeuLeuCysLeuL
               70                      90                     110
                .                       .                       .
     TCTCAAAGGTGCGTACCCAGCTGTGCCCGACACCATGTACCTGCCCCTGGCCACCTCCCC
     euSerLysValArgThrGlnLeuCysProThrProCysThrCysProTrpProProProA
              130                     150                     170
                .                       .                       .
     GATGCCCGCTGGGAGTACCCCTGGTGCTGGATGGCTGTGGCTGCTGCCGGGTATGTGCAC
     rgCysProLeuGlyValProLeuValLeuAspGlyCysGlyCysCysArgValCysAlaA
              190                     210                     230
                .                       .                       .
     GGCGGCTGGGGGAGCCCTGCGACCAACTCCACGTCTGCGACGCCAGCCAGGGCCTGGTCT
     rgArgLeuGlyGluProCysAspGlnLeuHisValCysAspAlaSerGlnGlyLeuValC
              250                     270                     290
                .                       .                       .
     GCCAGCCCGGGGCAGGACCCGGTGGCCGGGGGGCCCTGTGCCTCTTGGCAGAGGACGACA
     ysGlnProGlyAlaGlyProGlyGlyArgGlyAlaLeuCysLeuLeuAlaGluAspAspS
              310                     330                     350
                .                       .                       .
     GCAGCTGTGAGGTGAACGGCCGCCTGTATCGGGAAGGGGAGACCTTCCAGCCCCACTGCA
     erSerCysGluValAsnGlyArgLeuTyrArgGluGlyGluThrPheGlnProHisCysS
              370                     390                     410
                .                       .                       .
     GCATCCGCTGCCGCTGCGAGGACGGCGGCTTCACCTGCGTGCCGCTGTGCAGCGAGGATG
     erIleArgCysArgCysGluAspGlyGlyPheThrCysValProLeuCysSerGluAspV
              430                     450                     470
                .                       .                       .
     TGCGGCTGCCCAGCTGGGACTGCCCCCACCCCAGGAGGGTCGAGGTCCTGGGCAAGTGCT
     alArgLeuProSerTrpAspCysProHisProArgArgValGluValLeuGlyLysCysC
              490                     510                     530
                .                       .                       .
     GCCCTGAGTGGGTGTGCGGCCAAGGAGGGGGACTGGGGACCCAGCCCCTTCCAGCCCAAG
     ysProGluTrpValCysGlyGlnGlyGlyGlyLeuGlyThrGlnProLeuProAlaGlnG
              550                     570                     590
                .                       .                       .
     GACCCCAGTTTTCTGGCCTTGTCTCTTCCCTGCCCCCTGGTGTCCCTGCCCAGAATGGA
     lyProGlnPheSerGlyLeuValSerSerLeuProProGlyValProCysProGluTrpS
```

FIG.1A

```
                  610                     630                      650
        .          .          .          .          .          .          .
GCACGGCCTGGGGACCCTGCTCGACCACCTGTGGGCTGGGCATGGCCACCCGGGTGTCCA
erThrAlaTrpGlyProCysSerThrThrCysGlyLeuGlyMetAlaThrArgValSerA
                  670                     690                      710
        .          .          .          .          .          .          .
ACCAGAACCGCTTCTGCCGACTGGAGACCCAGCGCCGCCTGTGCCTGTCCAGGCCCTGCC
snGlnAsnArgPheCysArgLeuGluThrGlnArgArgLeuCysLeuSerArgProCysP
                  730                     750                      770
        .          .          .          .          .          .          .
CACCCTCCAGGGGTCGCAGTCCACAAAACAGTGCCTTCTAGAGCCGGGCTGGGAATGGGG
roProSerArgGlyArgSerProGlnAsnSerAlaPheEnd
                  790                     810                      830
        .          .          .          .          .          .          .

ACACGGTGTCCACCATCCCCAGCTGGTGGCCCTGTGCCTGGGCCCTGGGCTGATGGAAGA
                  850                     870                      890
        .          .          .          .          .          .          .
TGGTCCGTGCCCAGGCCCTTGGCTGCAGGCAACACTTTAGCTTGGGTCCACCATGCAGAA
                  910                     930                      950
        .          .          .          .          .          .          .
CACCAATATTAACACGCTGCCTGGTCTGTCTGGATCCCGAGGTATGGCAGAGGTGCAAGA
                  970                     990                     1010
        .          .          .          .          .          .          .
CCTAGTCCCCTTTCCTCTAACTCACTGCCTAGGAGGCTGGCCAAGGTGTCCAGGGTCCTC
                 1030                    1050                     1070
        .          .          .          .          .          .          .
TAGCCCACTCCCTGCCTACACACACAGCCTATATCAAACATGCACACGGGCGAGCTTTCT
                 1090                    1110                     1130
        .          .          .          .          .          .          .
CTCCGACTTCCCCTGGGCAAGAGATGGGACAAGCAGTCCCTTAATATTGAGGCTGCAGCA
                 1150                    1170                     1190
        .          .          .          .          .          .          .
GGTGCTGGGCTGGACTGGCCATTTTTCTGGGGGTAGGATGAAGAGAAGGCACACAGAGAT
                 1210                    1230                     1250
        .          .          .          .          .          .          .
TCTGGATCTCCTGCTGCCTTTTCTGGAGTTTGTAAAATTGTTCCTGAATACAAGCCTATG
                 1270
        .

CGTGAAAAAAAAAAAAAAAAAAAAAA
```

FIG.1B

```
                1                                                          50
CTGF-1aa   MTAASMGPVR VAFVVLLALC SRPAV.GQNC SGPCRCPDEP APRCPAGVSL
CTGF-3aa   ....MRGTPK THLLAFSLLC LLSKVRTQLC PTPCTCP.WP PPRCPLGVPL 51                                                        100
CTGF-1aa   VLDGCGCCRV CAKQLGELCT ERDPCDPHKG LFCDFGSPAN RKIGVC.TAK
CTGF-3aa   VLDGCGCCRV CARRLGEPCD QLHVCDASQG LVCQPGAGPG GRGALCLLAE 101                                                       150
CTGF-1aa   DGAPCIFGGT VYRSGESFQS SCKYQCTCLD GAVGCMPLCS MDVRLPSPDC
CTGF-3aa   DDSSCEVNGR LYREGETFQP HCSIRCRCED GGFTCVPLCS EDVRLPSWDC 151                                                       200
CTGF-1aa   PFPRRVKLPG KCCEEWVCDE PKDQTVVGPA LAAYRLEDTF GPDPTMIRAN
CTGF-3aa   PHPRRVEVLG KCCPEWVCGQ GGGLGTQPLP AQGPQFSGLV SSLPPGVP..

201                                                       250
CTGF-1aa   CLVQTTEWSA CSKTCGMGIS TRVTNDNASC RLEKQSRLCM VRPCEADLEE
CTGF-3aa   CPEWSTAWGP CSTTCGLGMA TRVSNQNRFC RLETQRRLCL SRPCPPSRGR 251                                                       300
CTGF-1aa   NIKKGKKCIR TPKISKPIKF ELSGCTSMKT YRAKFCGVCT DGRCCTPHRT
CTGF-3aa   SPQNSAF... .......... .......... .......... ..........

301                                                       350
CTGF-1aa   TTLPVEFKCP DGEVMKKNMM FIKTCACHYN CPGDNDIFES LYYRKMYGDM
CTGF-3aa   .......... .......... .......... .......... ..........

351
CTGF-1aa   A
CTGF-3aa
```

FIG.2

CONNECTIVE TISSUE GROWTH FACTOR (CTGF-3)

CROSS-REFERENCE TO RELATED APPLICATIONS

This application is a continuation of U.S. application Ser. No. 10/721,336, filed Nov. 26, 2003, which is a continuation of U.S. application Ser. No. 09/712,142, filed Nov. 15, 2000, which is a continuation of U.S. application Ser. No. 08/966,020, filed Nov. 7, 1997, which claims the benefit of the filing date of U.S. provisional Application No. 60/030,720, filed Nov. 8, 1996. Each of said applications is incorporated herein by reference it its entirety.

STATEMENT UNDER 37 C.F.R. §1.77(b)(5)

This application refers to a "Sequence Listing" listed below, which is provided as a text document. The document is entitled "PF319C3_SeqList.txt" (14,109 bytes, created Dec. 20, 2007), and is hereby incorporated by reference in its entirety herein.

BACKGROUND OF THE INVENTION

1. Field of the Invention

The present invention relates to a novel connective tissue growth factor. More specifically, isolated nucleic acid molecules are provided encoding a human connective tissue growth factor-3. Connective tissue growth factor-3 polypeptides are also provided, as are vectors, host cells, and recombinant methods for producing the same. Also provided are diagnostic and therapeutic methods for detecting and treating connective tissue related disorders.

2. Background Art

Growth factors are a class of secreted cysteine-rich polypeptides that stimulate target cells to proliferate, differentiate, and organize in developing tissues. The action of growth factors is dependent on their binding to specific receptors, which stimulate a signaling event within the cell. Examples of some well-studied growth factors include platelet-derived growth factor (PDGF), insulin-like growth factor (IGF-I), transforming growth factor beta (TGF-β), transforming growth factor alpha (TGF-α), epidermal growth factor (EGF), and fibroblast growth factor (FGF). This group of growth factors is important for normal growth, differentiation, morphogenesis of the cartilaginous skeleton of an embryo, and cell growth. Among some of the functions that have been reported for these growth factors are wound healing, tissue repair/regeneration, implant fixation, and stimulating bone mass increase.

PDGF is a cationic, heat-stable protein found in the alpha-granules of circulating platelets and is known to be a mitogen and chemotactic agent for connective tissue cells such as fibroblasts and smooth muscle cells. Because of the activities of this molecule, PDGF is believed to be a major factor involved in the normal healing of wounds and pathologically contributes to such diseases as atherosclerosis and fibrotic diseases. PDGF is a dimeric molecule consisting of an A chain and a B chain. The chains form heterodimers or homodimers and all combinations isolated to date are biologically active.

Studies on the role of various growth factors in tissue regeneration and repair have led to the discovery of PDGF-like proteins. These proteins share both immunological and biological activities with PDGF and can be blocked with antibodies specific to PDGF.

U.S. Pat. No. 5,408,040 to Grotendorst et al. (1995) discloses a PDGF-like protein called Connective Tissue Growth Factor (CTGF) that reportedly plays a significant role in the normal development, growth, and repair of human tissue. The discovery of the CTGF protein and the cloning of the cDNA encoding the protein was reportedly significant in that it was a previously unknown growth factor having mitogenic and chemotactic activities for connective tissue cells. Although the biological activity of CTGF was similar to that of PDGF, CTGF is the product of a gene unrelated to the A or B chain genes of PDGF.

Since CTGF is produced by endothelial and fibroblastic cells, both of which are present at the site of a wound, it is probable that CTGF functions as a growth factor in wound healing. Accordingly, it is believed that the CTGF polypeptide could be used as a therapeutic in cases in which there is impaired healing of skin wounds or where there is a need to augment the normal healing process.

Pathologically, CTGF may also be involved in diseases in which there is an overgrowth of connective tissue cells or an enhanced production of extracellular matrix components. Such diseases include cancer, fibrosis, and atherosclerosis. For example, it has been shown that CTGF gene expression is elevated in the skin of patients with systemic sclerosis (SSc). Igarashi et al., *J. Invest. Dermatol.* 105:280-284 (1995). CTGF gene expression has also recently been demonstrated in several fibrotic skin diseases, such as localized scleroderma, keloid scars, nodular fasciatus, and eosinophilic fasciatus, suggesting a pathogenic role for this molecule in skin fibrosis. Igarashi et al., *J. Invest. Dermatol.* 106:729-733 (1996). Oemar et al., *Circulation* 92 (8), Supp't 1, Abstract 0811 (October 1995) have reported that human CTGF is expressed at 5-10 fold higher levels in the aorta, a tissue prone to develop atherosclerosis, as compared to expression levels in internal mammary arteries, which are resistant to atherosclerosis. Their results suggest that hCTGF may play an essential role in the development and progression of atherosclerosis. Therapeutically, it has been reported in U.S. Pat. No. 5,408,040 to Grotendorst et al. (1995) that CTGF antibodies or fragments of the antibody could be used to neutralize the biological activity of CTGF in diseases where CTGF is inducing the overgrowth of tissue. Additionally, antibodies to CTGF polypeptide or fragments could be valuable as diagnostic tools to aid in the detection of diseases in which CTGF is a pathological factor. Id.

Due to the important role of CTGF in the development and repair of human tissue, as well as its role in the development and progression of various connective-tissue related disorders, there is a clear need in the art for the identification of new connective tissue growth factors that can be utilized in the development of diagnostics and therapeutics for various connective tissue related disorders.

BRIEF SUMMARY OF THE INVENTION

The present invention provides isolated nucleic acid molecules comprising a polynucleotide encoding the connective tissue growth factor-3 polypeptide having the amino acid sequence shown in SEQ ID NO:2 or the amino acid sequence encoded by the cDNA clone deposited in a bacterial host as ATCC™ Deposit Number 97756 on Oct. 10, 1996.

The present invention also relates to recombinant vectors, which include the isolated nucleic acid molecules of the present invention, and to host cells containing the recombinant vectors, as well as to methods of making such vectors and host cells and for using them for production of connective tissue growth factor-3 polypeptides or peptides by recombinant techniques.

The invention further provides an isolated connective tissue growth factor-3 polypeptide having an amino acid sequence encoded by a polynucleotide described herein.

The invention further provides methods for isolating antibodies that bind specifically to a connective tissue growth factor-3 polypeptide having an amino acid sequence as described herein. Such antibodies are useful diagnostically or therapeutically as described below.

The present invention also provides a screening method for identifying compounds capable of enhancing or inhibiting a cellular response induced by connective tissue growth factor-3, which involves contacting cells that express connective tissue growth factor-3 with the candidate compound, assaying a cellular response, and comparing the cellular response to a standard cellular response, the standard being assayed when contact is made in the absence of the candidate compound; whereby, an increased cellular response over the standard indicates that the compound is an agonist and a decreased cellular response over the standard indicates that the compound is an antagonist.

In another aspect, a screening assay for agonists and antagonists is provided, which involves determining the effect a candidate compound has on connective tissue growth factor-3 binding to the connective tissue growth factor-3 receptor. In particular, the method involves contacting the connective tissue growth factor-3 receptor with a connective tissue growth factor-3 polypeptide and a candidate compound and determining whether connective tissue growth factor-3 polypeptide binding to the connective tissue growth factor-3 receptor is increased or decreased due to the presence of the candidate compound.

The present inventors have discovered that connective tissue growth factor-3 is expressed in multiple human tissues, including, for example, ovary, heart, lung, skeletal muscle, adrenal medulla, adrenal cortex, thymus, prostate, small intestine, and colon, as well as in Hela cells. It is also expected that connective tissue growth factor-3 will be expressed in fibrotic human skin and liver. For a number of connective tissue disorders or clinical states, it is believed that significantly higher or lower levels of connective tissue growth factor-3 gene expression can be detected in certain tissues (e.g., ovary, testis, fibrotic skin and liver) or bodily fluids (e.g., serum, plasma, urine, synovial fluid or spinal fluid) taken from an individual having such a disorder, relative to a "standard" connective tissue growth factor-3 gene expression level, i.e., the connective tissue growth factor-3 expression level in tissue or bodily fluids from an individual not having the connective tissue related disorder. Thus, the invention provides a diagnostic method useful during diagnosis of a connective tissue related disorder, which involves: (a) assaying connective tissue growth factor-3 gene expression level in cells or body fluid of an individual; (b) comparing the connective tissue growth factor-3 gene expression level with a standard connective tissue related growth factor-3 gene expression level, whereby an increase or decrease in the assayed connective tissue growth factor-3 gene expression level compared to the standard expression level is indicative of a connective tissue related disorder.

An additional aspect of the invention is related to a method for treating an individual in need of an increased level of connective tissue growth factor-3 activity in the body comprising administering to such an individual a composition comprising a therapeutically effective amount of an isolated connective tissue growth factor-3 polypeptide of the invention or an agonist thereof.

A still further aspect of the invention is related to a method for treating an individual in need of a decreased level of connective tissue growth factor-3 activity in the body comprising, administering to such an individual a composition comprising a therapeutically effective amount of a connective tissue growth factor-3 antagonist. Preferred antagonists for use in the present invention are connective tissue growth factor-3-specific antibodies.

BRIEF DESCRIPTION OF THE DRAWINGS/FIGURES

FIGS. 1A and 1B show the nucleotide (SEQ ID NO:1) and deduced amino acid (SEQ ID NO:2) sequences of connective tissue growth factor-3. The protein has a leader sequence of about 19 amino acid residues (underlined) and a deduced molecular weight of about 26 kDa.

FIG. 2 shows the regions of similarity between the amino acid sequences of the connective tissue growth factor-3 protein (SEQ ID NO:2) and connective tissue growth factor-1 (SEQ ID NO:3).

Figure 3:
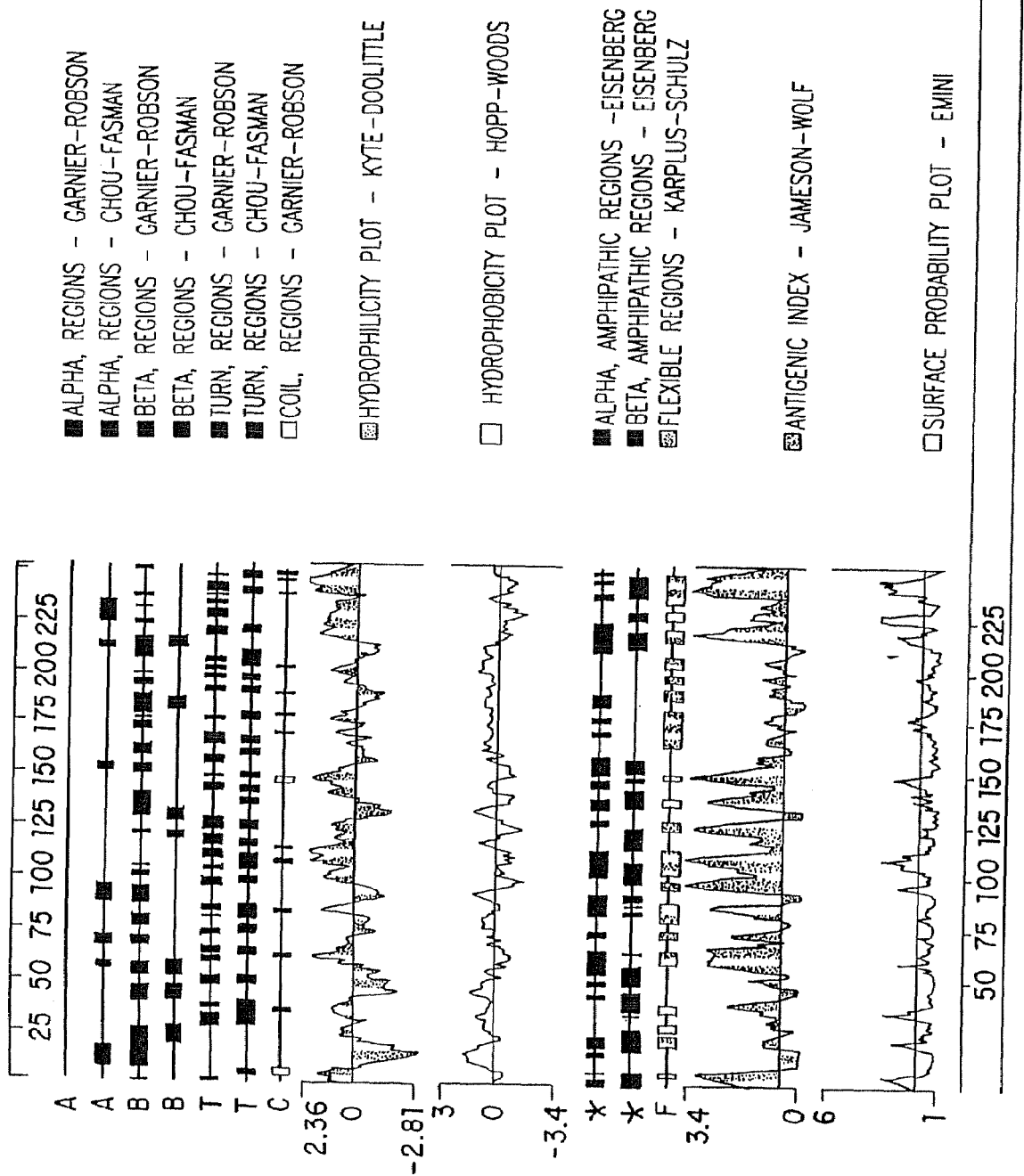

FIG. 3 shows an analysis of the connective tissue growth factor-3 amino acid sequence. Alpha, beta, turn, and coil regions; hydrophilicity and hydrophobicity; amphipathic regions; flexible regions; antigenic index and surface probability are shown. In the "Antigenic Index—Jameson-Wolf" graph, amino acid residues 55-68, 94-128, 134-158, and 215-249 in FIG. 1 correspond to the shown highly antigenic regions of the connective tissue growth factor-3 protein. These highly antigenic fragments in FIG. 1 correspond to the following fragments, respectively, in SEQ ID NO:2: amino acid residues about 36 to about 49, about 75 to about 109, about 115 to about 139, and about 196 to about 230.

DETAILED DESCRIPTION OF THE INVENTION

The present invention provides isolated nucleic acid molecules comprising a polynucleotide encoding a connective tissue growth factor-3 polypeptide having the amino acid sequence shown in SEQ ID NO:2, which was determined by sequencing a cloned cDNA. The connective tissue growth factor-3 protein of the present invention shares sequence homology with connective tissue growth factor-1 (FIG. 2) (SEQ ID NO:3). The nucleotide sequence shown in FIG. 1 (SEQ ID NO:1) was obtained by sequencing a cDNA clone, which was deposited Oct. 10, 1996 at the American Type Culture Collection, 10801 University Blvd., Manassas, Va. 20110-2209, USA, and given accession number 97756. The deposited clone is contained in the Uni-Zap XR vector (Stratagene, La Jolla, Calif.).

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleotide sequence in SEQ ID NO:1, a nucleic acid molecule of the present invention encoding a connective tissue growth factor-3 polypeptide may be obtained using standard cloning and screening procedures, such as those for cloning cDNAs using mRNA as starting material. Illustrative of the invention, the nucleic acid molecule described in SEQ ID NO:1 was discovered in a cDNA library derived from human osteoblasts. The gene was also identified in cDNA libraries from the following tissues: ovary, testis, heart, lung, skeletal muscle, adrenal medulla, adrenal cortex, thymus, prostate, small intestine, and colon.

The determined nucleotide sequence of the connective tissue growth factor-3 cDNA of SEQ ID NO:1 contains an open reading frame encoding a protein of 250 amino acid residues, a predicted leader sequence of about 19 amino acid residues, and a deduced molecular weight of about 26 kDa. The connective tissue growth factor-3 protein shown in SEQ ID NO:2 is about 44% identical and about 59% similar to human connective tissue growth factor-1 (SEQ ID NO:3) (FIG. 2).

The present invention also provides the mature form of the connective tissue growth factor-3 protein of the present invention. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature connective tissue growth factor-3 polypeptide having the amino acid sequence encoded by the cDNA clone contained in the host identified as ATCC™ Deposit No. 97756 and as shown in SEQ ID NO:2. By the mature connective tissue growth factor-3 protein having the amino acid sequence encoded by the cDNA clone contained in the host identified as ATCC™ Deposit 97756 is meant the mature form of the connective tissue growth factor-3 protein produced by expression in a mammalian cell (e.g., COS cells, as described below) of the complete open reading frame encoded by the human DNA sequence of the clone contained in the vector in the deposited host. As indicated below, the mature connective tissue growth factor-3 having the amino acid sequence encoded by the cDNA clone contained in ATCC™ Deposit No. 97756 may or may not differ from the predicted "mature" connective tissue growth factor-3 protein shown in SEQ ID NO:2 (amino acids from about 1 to about 231) depending on the accuracy of the predicted cleavage site based on computer analysis.

Methods for predicting whether a protein has a secretory leader as well as the cleavage point for that leader sequence are available. For instance, the methods of McGeoch (*Virus Res.* 3:271-286 (1985)) and von Heinje (*Nucleic Acids Res.* 14:4683-4690 (1986)) can be used. The accuracy of predicting the cleavage points of known mammalian secretory proteins for each of these methods is in the range of 75-80%. von Heinje, supra. However, the two methods do not always produce the same predicted cleavage point(s) for a given protein.

In the present case, the predicted amino acid sequence of the complete connective tissue growth factor-3 polypeptides of the present invention were analyzed by a computer program ("PSORT") (K. Nakai and M. Kanehisa, *Genomics* 14:897-911 (1992)), which is an expert system for predicting the cellular location of a protein based on the amino acid sequence. As part of this computational prediction of localization, the methods of McGeoch and von Heinje are incorporated. The analysis by the PSORT program predicted the cleavage site between amino acids −1 and 1 in SEQ ID NO:2. Thereafter, the complete amino acid sequences were further analyzed by visual inspection, applying a simple form of the (−1,−3) rule of von Heinje. von Heinje, supra. Thus, the leader sequence for the connective tissue growth factor-3 protein is predicted to consist of amino acid residues from about −19 to about −1 in SEQ ID NO:2, while the mature connective tissue growth factor-3 protein is predicted to consist of residues from about 1 to about 231.

As one of ordinary skill would appreciate, due to the possibilities of sequencing errors discussed above, as well as the variability of cleavage sites for leaders in different known proteins, the actual connective tissue growth factor-3 polypeptide encoded by the deposited cDNA comprises about 250 amino acids, but may be anywhere in the range of 235 to 265 amino acids; and the actual leader sequence of this protein is about 19 amino acids, but may be anywhere in the range of about 15 to about 25 amino acids.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) shown in SEQ ID NO:1; DNA molecules comprising the coding sequence for the mature connective tissue growth factor-3 protein; and DNA molecules which comprise a sequence substantially different from those described above but which, due to the degeneracy of the genetic code, still encode the connective tissue growth factor-3 protein. Of course, the genetic code is well known in the art. Thus, it would be routine for one skilled in the art to generate such degenerate variants.

In addition, the present inventors have identified the following cDNA clones related to extensive portions of SEQ ID NO:1: HSNAA66R (SEQ ID NO:10) and HSVAF40R (SEQ ID NO:11). The following public ESTs, which relate to portions of SEQ ID NO:1, have also been identified: AA385680 (SEQ ID NO:12) and C01967 (SEQ ID NO:13).

In another aspect, the invention provides isolated nucleic acid molecules encoding the connective tissue growth factor-3 polypeptide having an amino acid sequence encoded by the cDNA clone contained in the plasmid deposited as ATCC™ Deposit No. 97756 on Oct. 10, 1996. In a further embodiment, nucleic acid molecules are provided encoding the mature connective tissue growth factor-3 polypeptide or the full length connective tissue growth factor-3 polypeptide lacking the N-terminal methionine. The invention also provides an isolated nucleic acid molecule having the nucleotide sequence shown in SEQ ID NO:1 or the nucleotide sequence of the connective tissue growth factor-3 cDNA contained in the above-described deposited clone, or a nucleic acid molecule having a sequence complementary to one of the above sequences. Such isolated molecules, particularly DNA molecules, are useful as probes for gene mapping, by in situ hybridization with chromosomes, and for detecting expression of the connective tissue growth factor-3 gene in human tissue, for instance, by Northern blot analysis.

The present invention is further directed to fragments of the isolated nucleic acid molecules described herein. By a fragment of an isolated nucleic acid molecule having the nucleotide sequence of the deposited cDNA or the nucleotide sequence shown in SEQ ID NO:1 is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1125, 1150, 1175, 1200, 1225, 1250, or 1275 nt in length are also useful according to the present invention as are fragments corresponding to most, if not all, of the nucleotide sequence of the deposited cDNA or as shown in SEQ ID NO:1. By a fragment at least 20 nt in length, for example, is intended fragments which include 20 or more contiguous bases from the nucleotide sequence of the deposited cDNA or the nucleotide sequence as shown in SEQ ID NO:1.

Preferred nucleic acid fragments of the present invention include nucleic acid molecules encoding epitope-bearing portions of the connective tissue growth factor-3 protein. In particular, such nucleic acid fragments of the present invention include nucleic acid molecules encoding: a polypeptide comprising amino acid residues from about 55 to about 68 in FIG. 1 (about 36 to about 49 in SEQ ID NO:2); a polypeptide comprising amino acid residues from about 94 to about 128 in FIG. 1 (about 75 to about 109 in SEQ ID NO:2); a polypeptide comprising amino acid residues from about 134 to about 158 in FIG. 1 (about 115 to about 139 in SEQ ID NO:2); and a polypeptide comprising amino acid residues from about 215 to about 249 in FIG. 1 (about 196 to about 230 in SEQ ID NO:2). The inventors have determined that the above polypeptide fragments are antigenic regions of the connective tissue growth factor-3 protein. Methods for determining other such epitope-bearing portions of the connective tissue growth factor-3 protein are described in detail below.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clone contained in ATCC™ Deposit 97756. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30-70 nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in FIG. 1 (SEQ ID NO:1)). Of course, a polynucleotide which hybridizes only to a poly A sequence (such as the 3' terminal poly(A) tract of the connective tissue growth factor-3 cDNA shown in FIG. 1 (SEQ ID NO:1)), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode a connective tissue growth factor-3 polypeptide may include, but are not limited to those encoding the amino acid sequence of the mature polypeptide, by itself; the coding sequence for the mature polypeptide and additional sequences, such as those encoding the about 19 amino acid leader or secretory sequence, such as a pre-, or pro- or prepro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities. Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al., *Proc. Natl. Acad. Sci. USA* 86:821-824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37: 767 (1984). As discussed below, other such fusion proteins include the connective tissue growth factor-3 fused to Fc at the N- or C-terminus.

The present invention further relates to variants of the nucleic acid molecules of the present invention, which encode portions, analogs, or derivatives of the connective tissue growth factor-3 protein. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Such variants include those produced by nucleotide substitutions, deletions, or additions, which may involve one or more nucleotides. The variants may be altered in coding regions, non-coding regions, or both. Alterations in the coding regions may produce conservative or non-conservative amino acid substitutions, deletions, or additions. Especially preferred among these are silent substitutions, additions, and deletions, which do not alter the properties and activities of the connective tissue growth factor-3 protein or portions thereof. Also especially preferred in this regard are conservative substitutions.

Further embodiments of the invention include isolated nucleic acid molecules comprising a polynucleotide having a nucleotide sequence at least 95% identical, and more preferably at least 96%, 97%, 98%, or 99% identical to (a) a nucleotide sequence encoding the polypeptide having the amino acid sequence in SEQ ID NO:2; (b) a nucleotide sequence encoding the polypeptide having the amino acid sequence in SEQ ID NO:2, but lacking the N-terminal methionine; (c) a nucleotide sequence encoding the polypeptide having the amino acid sequence at positions from about 1 to about 231 in SEQ ID NO:2; (d) a nucleotide sequence encoding the polypeptide having the amino acid sequence encoded by the cDNA clone contained in ATCC™ Deposit No. 97756; (e) a nucleotide sequence encoding the mature connective tissue growth factor-3 polypeptide having the amino acid sequence encoded by the cDNA clone contained in ATCC™ Deposit No. 97756; or (f) a nucleotide sequence complementary to any of the nucleotide sequences in (a), (b), (c), (d), or (e).

By a polynucleotide having a nucleotide sequence at least, for example, 95% "identical" to a reference nucleotide sequence encoding a connective tissue growth factor-3 polypeptide is intended that the nucleotide sequence of the polynucleotide is identical to the reference sequence except that the polynucleotide sequence may include up to five point mutations per each 100 nucleotides of the reference nucleotide sequence encoding the connective tissue growth factor-3 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98%, or 99% identical to, for instance, the nucleotide sequence shown in FIG. 1 or to the nucleotides sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2: 482-489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 95%, 96%, 97%, 98%, or 99% identical to the nucleic acid sequence shown in SEQ ID NO:1 or to the nucleic acid sequence of the deposited cDNA, irrespective of whether they encode a polypeptide having connective tissue growth factor-3 activity. This is because even where a particular nucleic acid molecule does not encode a polypeptide having connective tissue growth factor-3 activity, one of skill in the art would still know how to use the nucleic acid molecule, for instance, as a hybridization probe or a polymerase chain reaction (PCR) primer. Uses of the nucleic acid molecules of the present invention that do not encode a polypeptide having connective tissue growth factor-3 activity include, inter alia: (1) isolating the connective tissue growth factor-3 gene or allelic variants thereof in a cDNA library; (2) in situ hybridization (e.g., "FISH") to metaphase chromosomal spreads to provide precise chromosomal location of the connective tissue growth factor-3 gene, as described in Verma et al., Human Chromosomes: A Manual of Basic Techniques, Pergamon Press, New York (1988); and Northern Blot analysis for detecting connective tissue growth factor-3 mRNA expression in specific tissues.

Preferred, however, are nucleic acid molecules having sequences at least 95%, 96%, 97%, 98%, or 99% identical to the nucleic acid sequence shown in FIG. 1 (SEQ ID NO:1) or to the nucleic acid sequence of the deposited cDNA which do, in fact, encode a polypeptide having connective tissue growth factor-3 protein activity. By "a polypeptide having connective tissue growth factor-3 activity" is intended polypeptides exhibiting connective tissue growth factor-3 activity in a particular biological assay. For example, it is believed that connective tissue growth factor-3 will have chemotactic and mitogenic activity for connective tissue cells, similar to platelet-derived growth factor (PDGF). Assays to test these activities are described in DiCorleto, P. E., *Exp. Cell. Res.* 153:167-172 (1984). In addition, it is believed that connective tissue growth factor-3 activity will include an increased synthesis of extracellular matrix/connective tissue components, such as, e.g., collagen, fibronectin, PA1-1, syndecan, and elastin. This activity can be tested by Northern and Western blot or ELISA analyses after treatment of cultured cells with CTGF-3 protein.

Of course, due to the degeneracy of the genetic code, one of ordinary skill in the art will immediately recognize that a large number of the nucleic acid molecules having a sequence at least 95%, 96%, 97%, 98%, or 99% identical to the nucleic acid sequence of the deposited cDNA or the nucleic acid sequence shown in FIG. 1 (SEQ ID NO:1) will encode a polypeptide "having connective tissue growth factor-3 protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having connective tissue growth factor-3 protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al., "Deciphering the Message in Protein Sequences: Tolerance to Amino Acid Substitutions," *Science* 247:1306-1310 (1990), wherein the authors indicate that proteins are surprisingly tolerant of amino acid substitutions.

Vectors and Host Cells

The present invention also relates to vectors that include the isolated DNA molecules of the present invention, host cells that are genetically engineered with the recombinant vectors, and the production of connective tissue growth factor-3 polypeptides or fragments thereof by recombinant techniques.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the *E. coli* lac, trp, and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells; insect cells such as *Drosophila* S2 and *Spodoptera* Sf9 cells; animal cells such as CHO, COS, and Bowes melanoma cells; and plant cells. Appropriate culture mediums and conditions for the above-described host cells are known in the art.

Among vectors preferred for use in bacteria include pQE70, pQE60, and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRrT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected, and purified in the advantageous manner described. This is the case when the Fc portion proves to be a hindrance to use in therapy and diagnosis, for example, when the fusion protein is to be used as antigen for immunizations. In drug discovery, for example, human proteins, such as, the hIL5-receptor, have been fused with Fc portions for the purpose of high-throughput screening assays to identify antagonists of hIL-5. See, D. Bennett et al., *Journal of Molecular Recognition* 8:52-58 (1995) and K. Johanson et al., *The Journal of Biological Chemistry* 270:9459-9471 (1995).

The connective tissue growth factor-3 protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Connective Tissue Growth Factor-3 Polypeptides and Fragments

The invention further provides an isolated connective tissue growth factor-3 polypeptide having the amino acid sequence encoded by the deposited cDNA, or the amino acid sequence in SEQ ID NO:2, or a peptide or polypeptide comprising a portion of the above polypeptides.

It will be recognized in the art that some amino acid sequences of the connective tissue growth factor-3 polypeptide can be varied without significant effect of the structure or function of the protein. If such differences in sequence are contemplated, it should be remembered that there will be critical areas on the protein which determine activity.

Thus, the invention further includes variations of the connective tissue growth factor-3 polypeptide that show substantial connective tissue growth factor-3 polypeptide activity or that include regions of connective tissue growth factor-3 protein, such as the protein portions discussed below. Such mutants include deletions, insertions, inversions, repeats, and type substitutions. As indicated above, guidance concerning which amino acid changes are likely to be phenotypically silent can be found in Bowie, J. U. et al., "Deciphering the Message in Protein Sequences: Tolerance to Amino Acid Substitutions," *Science* 247:1306-1310 (1990).

Thus, the fragment, derivative or analog of the polypeptide of SEQ ID NO: 2, or that encoded by the deposited cDNA, may be: (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the connective tissue growth factor-3 protein. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331-340 (1967); Robbins et al., *Diabetes* 36:838-845 (1987); Cleland et al. *Crit. Rev. Therapeutic Drug Carrier Systems* 10:307-377 (1993)).

As indicated, changes are preferably of a minor nature, such as conservative amino acid substitutions that do not significantly affect the folding or activity of the protein (see Table 1).

TABLE 1

Conservative Amino Acid Substitutions

| | |
|---|---|
| Aromatic | Phenylalinine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Blutamic Acid |
| Small | Alanine |
| | Serine |
| | Threonine |
| | Glycine |

Of course, the number of amino acid substitutions a skilled artisan would make depends on many factors, including those described above. Generally speaking, the number of amino acid substitutions for any given connective tissue growth factor-3 polypeptide will not be more than 50, 40, 30, 25, 20, 15, 10, 5, or 3.

Amino acids in the connective tissue growth factor-3 polypeptide of the present invention that are essential for function can be identified by methods known in the art, such as site-directed mutagenesis or alanine-scanning mutagenesis (Cunningham and Wells, *Science* 244:1081-1085 (1989)). The latter procedure introduces single alanine mutations at every residue in the molecule. The resulting mutant molecules are then tested for biological activity such as receptor binding or in vitro proliferative activity. Sites that are critical for protein activity can also be determined by structural analysis such as crystallization, nuclear magnetic resonance or photoaffinity labeling (Smith et al., *J. Mol. Biol.* 224:899-904 (1992) and de Vos et al. *Science* 255:306-312 (1992)).

The polypeptides of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell or a native source. For example, a recombinantly produced version of the connective tissue growth factor-3 polypeptide can be substantially purified by the one-step method described in Smith and Johnson, *Gene* 67:31-40 (1988).

The polypeptides of the present invention include the polypeptide encoded by the deposited cDNA including the leader; the mature polypeptide encoded by the deposited cDNA minus the leader (i.e., the mature protein); a polypeptide comprising amino acids about −19 to about 231 in SEQ ID NO:2; a polypeptide comprising amino acids about −18 to about 231 in SEQ ID NO:2; a polypeptide comprising amino acids about 1 to about 231 in SEQ ID NO:2; as well as polypeptides which are at least 95% identical, more preferably at least 96%, 97%, 98%, or 99% identical to those described above, and also include portions of such polypeptides with at least 30 amino acids and more preferably at least 50 amino acids.

By a polypeptide having an amino acid sequence at least, for example, 95% "identical" to a reference amino acid sequence of a connective tissue growth factor-3 polypeptide is intended that the amino acid sequence of the polypeptide is identical to the reference sequence except that the polypeptide sequence may include up to five amino acid alterations per each 100 amino acids of the reference amino acid of the connective tissue growth factor-3 polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 95%, 96%, 97%, 98% or 99% identical to, for instance, the amino acid sequence shown in SEQ ID NO:2 or to the amino acid sequence encoded by the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptide of the present invention could be used as a molecular weight marker on SDS-PAGE gels or on molecular sieve gel filtration columns using methods well known to those of skill in the art.

As described in detail below, the polypeptides of the present invention can also be used to raise polyclonal and monoclonal antibodies, which are useful in assays for detecting connective tissue growth factor-3 protein expression as described below or as agonists and antagonists capable of enhancing or inhibiting connective tissue growth factor-3 protein function. Further, such polypeptides can be used in the yeast two-hybrid system to "capture" connective tissue growth factor-3 protein binding proteins which are also candidate agonist and antagonist according to the present invention. The yeast two hybrid system is described in Fields and Song, *Nature* 340:245-246 (1989).

In another aspect, the invention provides a peptide or polypeptide comprising an epitope-bearing portion of a polypeptide of the invention. The epitope of this polypeptide portion is an immunogenic or antigenic epitope of a polypeptide described herein. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998-4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe et al., "Antibodies That React With Predetermined Sites on Proteins," *Science* 219:660-666 (1983). Peptides capable of eliciting protein-reactive sera are frequently represented in the primary sequence of a protein, can be characterized by a set of simple chemical rules, and are confined neither to the immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, peptides, especially those containing proline residues, usually are effective. Sutcliffe et al., supra, at 661. For instance, 18 of 20 peptides designed according to these guidelines, containing 8-39 residues covering 75% of the sequence of the influenza virus hemagglutinin HA1 polypeptide chain, induced antibodies that reacted with the HA protein or intact virus; and 12/12 peptides from the MuLV polymerase and 18/18 from the rabies glycoprotein induced antibodies that precipitated the respective proteins. Antigenic epitope-bearing peptides and polypeptides of the invention are therefore useful to raise antibodies, including monoclonal antibodies, that bind specifically to a polypeptide of the invention. Thus, a high proportion of hybridomas, obtained by fusion of spleen cells from donors immunized with an antigen epitope-bearing peptide, generally secrete antibody, reactive with the native protein. Sutcliffe et al., supra, at 663. The antibodies raised by antigenic epitope-bearing peptides or polypeptides are useful to detect the mimicked protein, and antibodies to different peptides may be used for tracking the fate of various regions of a protein precursor which undergo post-translational processing. The peptides and anti-peptide antibodies may be used in a variety of qualitative or quantitative assays for the mimicked protein, for instance, in competition assays since it has been shown that even short peptides (e.g., about 9 amino acids) can bind and displace the larger peptides in immunoprecipitation assays. See, for instance, Wilson et al., *Cell* 37:767-778 (1984) at 777. The anti-peptide antibodies of the invention also are useful for purification of the mimicked protein, for instance, by adsorption chromatography using methods well known in the art.

Antigenic epitope-bearing peptides and polypeptides of the invention preferably contain a sequence of at least seven, more preferably at least nine, and most preferably between about 15 to about 30 amino acids contained within the amino acid sequence of a polypeptide of the invention. However, peptides or polypeptides comprising a larger portion of an amino acid sequence of a polypeptide of the invention, containing about 30 to about 50 amino acids, or any length up to and including the entire amino acid sequence of a polypeptide of the invention, also are considered epitope-bearing peptides or polypeptides of the invention and also are useful for inducing antibodies that react with the mimicked protein.

Non-limiting examples of antigenic polypeptides or peptides that can be used to generate connective tissue growth factor-3-specific antibodies include: a polypeptide comprising amino acid residues from about 55 to about 68 in FIG. 1 (about 36 to about 49 in SEQ ID NO:2); a polypeptide comprising amino acid residues from about 94 to about 128 in FIG. 1 (about 75 to about 109 in SEQ ID NO:2); a polypeptide comprising amino acid residues from about 134 to about 158 in FIG. 1 (about 115 to about 139 in SEQ ID NO:2); and a polypeptide comprising amino acid residues from about 215 to about 249 in FIG. 1 (about 196 to about 230 in SEQ ID NO: 2). As indicated above, the inventors have determined that the above polypeptide fragments are antigenic regions of the connective tissue growth factor-3 protein.

The epitope-bearing peptides and polypeptides of the invention may be produced by any conventional means. Houghten, R. A., "General Method for the Rapid Solid-Phase Synthesis of Large Numbers of Peptides: Specificity of Antigen-Antibody Interaction at the Level of Individual Amino Acids," *Proc. Natl. Acad. Sci. USA* 82:5131-5135 (1985). This "Simultaneous Multiple Peptide Synthesis (SMPS)" process is further described in U.S. Pat. No. 4,631,211 to Houghten et al. (1986).

Epitope-bearing peptides and polypeptides of the invention are used to induce antibodies according to methods well known in the art. See, for instance, Sutcliffe et al., supra; Wilson et al., supra; Chow, M. et al., *Proc. Natl. Acad. Sci. USA* 82:910-914 (1985); and Bittle, F. J. et al., *J. Gen. Virol.* 66:2347-2354 (1985). Generally, animals may be immunized with free peptide; however, anti-peptide antibody titer may be boosted by coupling of the peptide to a macromolecular carrier, such as keyhole limpet hemocyanin (KLH) or tetanus toxoid. For instance, peptides containing cysteine may be coupled to carrier using a linker such as m-maleimidobenzoyl-N-hydroxysuccinimide ester (MBS), while other peptides may be coupled to carrier using a more general linking agent such as glutaraldehyde. Animals such as rabbits, rats, and mice are immunized with either free or carrier-coupled peptides, for instance, by intraperitoneal and/or intradermal injection of emulsions containing about 100 g peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Immunogenic epitope-bearing peptides of the invention, i.e., those parts of a protein that elicit an antibody response when the whole protein is the immunogen, are identified according to methods known in the art. For instance, Geysen et al., supra, disclose a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner, a peptide bearing an immunogenic epitope of a desired protein may be identified routinely by one of ordinary skill in the art. For instance, the immunologically important epitope in the coat protein of foot-and-mouth disease virus was located by Geysen et al. with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

Further still, U.S. Pat. No. 5,194,392 to Geysen (1990) describes a general method of detecting or determining the sequence of monomers (amino acids or other compounds) which is a topological equivalent of the epitope (i.e., a "mimotope"), which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) entitled "Peralkylated Oligopeptide Mixtures" discloses linear $C_1$-$C_7$-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

The entire disclosure of each document cited in this section on "Polypeptides and Peptides" is hereby incorporated herein by reference.

As one of skill in the art will appreciate, connective tissue growth factor-3 polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., Nature 331:84-86 (1988)). Fusion proteins that have a disulfide-linked dimeric structure due to the IgG part can also be more efficient in binding and neutralizing other molecules than the monomeric connective tissue growth factor-3 protein or protein fragment alone (Fountoulakis et al., J Biochem 270:3958-3964 (1995)).

Diagnosis and Prognosis of Connective Tissue Related Disorders

It is believed that certain tissues in mammals with various connective-tissue related disorders express significantly altered levels of the connective tissue growth factor-3 protein and mRNA encoding the connective tissue growth factor-3 protein, when compared to a corresponding "standard" mammal, i.e., a mammal of the same species not having the disorder. By "connective tissue related disorders" is intended any disease or condition that is caused by, associated with, or characterized by an over or under growth of connective tissue cells. Some non-limiting examples of such disorders include cancer, arthritis, fibrosis, atherosclerosis, and osteoporosis.

For example, it is believed that enhanced levels of the connective tissue growth factor-3 protein can be detected in certain body fluids (e.g., sera, plasma, urine, and spinal fluid) or tissues from mammals with cancer, fibrosis, arthritis, or atherosclerosis when compared to sera from mammals of the same species not having these diseases. Thus, the invention provides a diagnostic method useful during diagnosis of connective-tissue related disorders, such as cancer, fibrosis, arthritis, or atherosclerosis, which involves assaying the expression level of the gene encoding the connective tissue growth factor-3 protein in mammalian cells or body fluid and comparing the gene expression level with a standard connective tissue growth factor-3 gene expression level, whereby an increase in the gene expression level over the standard is indicative of these diseases.

Where a diagnosis of any of these diseases has already been made according to conventional methods, the present invention is also useful as a prognostic indicator, whereby patients exhibiting enhanced connective tissue growth factor-3 gene expression will experience a worse clinical outcome relative to patients expressing the gene at a lower level.

It is also believed that decreased levels of the connective tissue growth factor-3 protein can be detected in certain body fluids (e.g., sera, plasma, urine, and spinal fluid) or tissues from mammals with certain connective-tissue related disorders, such as osteoporosis, when compared to sera from mammals of the same species not having the disease. Thus, the invention provides a diagnostic method useful during diagnosis of connective-tissue related disorders, such as osteoporosis, which involves assaying the expression level of the gene encoding the connective tissue growth factor-3 protein in mammalian cells or body fluid and comparing the gene expression level with a standard connective tissue growth factor-3 gene expression level, whereby a decrease in the gene expression level over the standard is indicative of the disease.

By "assaying the expression level of the gene encoding the connective tissue growth factor-3 protein" is intended qualitatively or quantitatively measuring or estimating the level of the connective tissue growth factor-3 protein or the level of the mRNA encoding the connective tissue growth factor-3 protein in a first biological sample either directly (e.g., by determining or estimating absolute protein level or mRNA level) or relatively (e.g., by comparing to the connective tissue growth factor-3 protein level or mRNA level in a second biological sample).

Preferably, the connective tissue growth factor-3 protein level or mRNA level in the first biological sample is measured or estimated and compared to a standard connective tissue growth factor-3 protein level or mRNA level, the standard being taken from a second biological sample obtained from an individual not having the connective-tissue related disorder. As will be appreciated in the art, once a standard connective tissue growth factor-3 protein level or mRNA level is known, it can be used repeatedly as a standard for comparison.

By "biological sample" is intended any biological sample obtained from an individual, cell line, tissue culture, or other source which contains connective tissue growth factor-3 protein or mRNA. Biological samples include mammalian body fluids (such as sera, plasma, urine, synovial fluid and spinal fluid) which contain secreted mature connective tissue growth factor-3 protein, and ovarian, testicular, prostate, heart, placenta, pancreas liver, spleen, lung, breast and umbilical tissue. Methods for obtaining tissue biopsies and body fluids from mammals are well known in the art. Where the biological sample is to include mRNA, a tissue biopsy is the preferred source.

The present invention is useful for detecting cancer in mammals. In particular, the invention is useful during diagnosis of the following types of cancers in mammals: breast, ovarian, cervical, prostate, bone, liver, lung, pancreatic, and splenic. Preferred mammals include monkeys, apes, cats, dogs, cows, pigs, horses, rabbits and humans. Particularly preferred are humans.

Total cellular RNA can be isolated from a biological sample using any suitable technique such as the single-step guanidinium-thiocyanate-phenol-chloroform method described in Chomczynski and Sacchi, *Anal. Biochem.* 162: 156-159 (1987). Levels of mRNA encoding the connective tissue growth factor-3 protein are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Northern blot analysis can be performed as described in Harada et al., *Cell* 63:303-312 (1990). Briefly, total RNA is prepared from a biological sample as described above. For the Northern blot, the RNA is denatured in an appropriate buffer (such as glyoxal/dimethyl sulfoxide/sodium phosphate buffer), subjected to agarose gel electrophoresis, and transferred onto a nitrocellulose filter. After the RNAs have been linked to the filter by a UV linker, the filter is prehybridized in a solution containing formamide, SSC, Denhardt's solution, denatured salmon sperm, SDS, and sodium phosphate buffer. Connective tissue growth factor-3 protein cDNA labeled according to any appropriate method (such as the $^{32}$P-multiprimed DNA labeling system (Amersham)) is used as probe. After hybridization overnight, the filter is washed and exposed to x-ray film. cDNA for use as a probe according to the present invention is described in the sections above, and will preferably be at least 15 bp in length.

S1 mapping can be performed as described in Fujita et al., *Cell* 49:357-367 (1987). To prepare probe DNA for use in S1 mapping, the sense strand of the above-described cDNA is used as a template to synthesize labeled antisense DNA. The antisense DNA can then be digested using an appropriate restriction endonuclease to generate further DNA probes of a desired length. Such antisense probes are useful for visualizing protected bands corresponding to the target mRNA (i.e., mRNA encoding the connective tissue growth factor-3 protein). Northern blot analysis can be performed as described above.

Preferably, levels of mRNA encoding the connective tissue growth factor-3 protein are assayed using the RT-PCR method described in Makino et al., *Technique* 2:295-301 (1990). By this method, the radioactivities of the "amplicons" in the polyacrylamide gel bands are linearly related to the initial concentration of the target mRNA. Briefly, this method involves adding total RNA isolated from a biological sample in a reaction mixture containing a RT primer and appropriate buffer. After incubating for primer annealing, the mixture can be supplemented with a RT buffer, dNTPs, DTT, RNase inhibitor and reverse transcriptase. After incubation to achieve reverse transcription of the RNA, the RT products are then subject to PCR using labeled primers. Alternatively, rather than labeling the primers, a labeled dNTP can be included in the PCR reaction mixture. PCR amplification can be performed in a DNA thermal cycler according to conventional techniques. After a suitable number of rounds to achieve amplification, the PCR reaction mixture is electrophoresed on a polyacrylamide gel. After drying the gel, the radioactivity of the appropriate bands (corresponding to the mRNA encoding the connective tissue growth factor-3 protein)) is quantified using an imaging analyzer. RT and PCR reaction ingredients and conditions, reagent and gel concentrations, and labeling methods are well known in the art. Variations on the RT-PCR method will be apparent to the skilled artisan.

Any set of oligonucleotide primers that will amplify reverse transcribed target mRNA can be used and can be designed as described in the sections above.

Assaying connective tissue growth factor-3 protein levels in a biological sample can occur using any art-known method. Preferred for assaying connective tissue growth factor-3 protein levels in a biological sample are antibody-based techniques. For example, connective tissue growth factor-3 protein expression in tissues can be studied with classical immunohistological methods. In these, the specific recognition is provided by the primary antibody (polyclonal or monoclonal) but the secondary detection system can utilize fluorescent, enzyme, or other conjugated secondary antibodies. As a result, an immunohistological staining of tissue section for pathological examination is obtained. Tissues can also be extracted, e.g., with urea and neutral detergent, for the liberation of connective tissue growth factor-3 protein for Western blot or dot/slot assay (Jalkanen, M., et al., *J. Cell. Biol.* 101: 976-985 (1985); Jalkanen, M., et al., *J. Cell. Biol.* 105:3087-3096 (1987)). In this technique, which is based on the use of cationic solid phases, quantitation of connective tissue growth factor-3 protein can be accomplished using isolated connective tissue growth factor-3 protein as a standard. This technique can also be applied to body fluids. With these samples, a molar concentration of connective tissue growth factor-3 protein will aid to set standard values of connective tissue growth factor-3 protein content for different body fluids, like serum, plasma, urine, spinal fluid, etc. The normal appearance of connective tissue growth factor-3 protein amounts can then be set using values from healthy individuals, which can be compared to those obtained from a test subject.

Other antibody-based methods useful for detecting connective tissue growth factor-3 protein gene expression include immunoassays, such as the enzyme linked immunosorbent assay (ELISA) and the radioimmunoassay (RIA). For example, a connective tissue growth factor-3 protein-specific monoclonal antibody can be used both as an immunoabsorbent and as an enzyme-labeled probe to detect and quantify the connective tissue growth factor-3 protein. The amount of connective tissue growth factor-3 protein present in the sample can be calculated by reference to the amount present in a standard preparation using a linear regression computer algorithm. Such an ELISA for detecting a tumor antigen is described in Iacobelli et al., *Breast Cancer Research and Treatment* 11:19-30 (1988). In another ELISA assay, two distinct specific monoclonal antibodies can be used to detect connective tissue growth factor-3 protein in a body fluid. In this assay, one of the antibodies is used as the immunoabsorbent and the other as the enzyme-labeled probe.

The above techniques may be conducted essentially as a "one-step" or "two-step" assay. The "one-step" assay involves contacting connective tissue growth factor-3 protein with immobilized antibody and, without washing, contacting the mixture with the labeled antibody. The "two-step" assay involves washing before contacting the mixture with the labeled antibody. Other conventional methods may also be employed as suitable. It is usually desirable to immobilize one component of the assay system on a support, thereby allowing other components of the system to be brought into contact with the component and readily removed from the sample.

Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labelled antibody/substrate reaction. Besides enzymes, other suitable labels include radioisotopes, such as iodine ($^{125}$I, $^{131}$I, carbon ($^{14}$C), sulphur ($^{35}$S), tritium ($^{3}$H), indium ($^{112}$In), and technetium ($^{99m}$Tc), and fluorescent labels, such as fluorescein and rhodamine, and biotin.

In addition to assaying connective tissue growth factor-3 protein levels in a biological sample obtained from an individual, connective tissue growth factor-3 protein can also be detected in vivo by imaging. Antibody labels or markers for in vivo imaging of connective tissue growth factor-3 protein include those detectable by X-radiography, NMR, or ESR. For X-radiography, suitable labels include radioisotopes such as barium or cesium, which emit detectable radiation, but are not overtly harmful to the subject. Suitable markers for NMR and ESR include those with a detectable characteristic spin, such as deuterium, which may be incorporated into the antibody by labeling of nutrients for the relevant hybridoma.

A connective tissue growth factor-3 protein-specific antibody or antibody fragment which has been labeled with an appropriate detectable imaging moiety, such as a radioisotope (for example, $^{131}$I, $^{112}$In, $^{99m}$Tc), a radio-opaque substance, or a material detectable by nuclear magnetic resonance, is introduced (for example, parenterally, subcutaneously or intraperitoneally) into the mammal to be examined for cancer. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody or antibody fragment will then preferentially accumulate at the location of cells which contain connective tissue growth factor-3 protein. In vivo tumor imaging is described in S. W. Burchiel et al., "Immunopharmacokinetics of Radiolabelled Antibodies and Their Fragments" (Chapter 13 in *Tumor Imaging: The Radiochemical Detection of Cancer*, eds., S. W. Burchiel and B. A. Rhodes, Masson Publishing, Inc. (1982)).

Connective tissue growth factor-3-protein specific antibodies for use in the present invention can be raised against the intact connective tissue growth factor-3 protein or an antigenic polypeptide fragment thereof, which may be presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules as well as antibody fragments (such as, for example, Fab and F(ab')$_2$ fragments) which are capable of specifically binding to connective tissue growth factor-3 protein. Fab and F(ab')$_2$ fragments lack the Fc fragment of intact antibody, clear more rapidly from the circulation, and may have less non-specific tissue binding of an intact antibody (Wahl et al., *J. Nucl. Med.* 24:316-325 (1983)). Thus, these fragments are preferred.

The antibodies of the present invention may be prepared by any of a variety of methods. For example, cells expressing the connective tissue growth factor-3 protein or an antigenic fragment thereof can be administered to an animal in order to induce the production of sera containing polyclonal antibodies. In a preferred method, a preparation of connective tissue growth factor-3 protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or connective tissue growth factor-3 protein binding fragments thereof). Such monoclonal antibodies can be prepared using hybridoma technology (Kohler et al., *Nature* 256:495 (1975); Kohler et al., *Eur. J. Immunol.* 6:511 (1976); Kohler et al., *Eur. J. Immunol.* 6:292 (1976); Hammerling et al., In: *Monoclonal Antibodies and T-Cell Hybridomas*, Elsevier, N.Y., pp. 563-681 (1981)). In general, such procedures involve immunizing an animal (preferably a mouse) with a connective tissue growth factor-3 protein antigen or, more preferably, with a connective tissue growth factor-3 protein-expressing cell. Suitable cells can be recognized by their capacity to bind anti-connective tissue growth factor-3 protein antibody. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 g/ml of streptomycin. The splenocytes of such mice are extracted and fused with a suitable myeloma cell line. Any suitable myeloma cell line may be employed in accordance with the present invention; however, it is preferable to employ the parent myeloma cell line (SP$_2$O), available from the American Type Culture Collection, Manassas, Va. After fusion, the resulting hybridoma cells are selectively maintained in HAT medium, and then cloned by limiting dilution as described by Wands et al. (*Gastroenterology* 80:225-232 (1981)). The hybridoma cells obtained through such a selection are then assayed to identify clones which secrete antibodies capable of binding the connective tissue growth factor-3 protein antigen.

Alternatively, additional antibodies capable of binding to the connective tissue growth factor-3 protein antigen may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, connective tissue growth factor-3-protein specific antibodies are used to immunize an animal, preferably a mouse. The splenocytes of such an animal are then used to produce hybridoma cells, and the hybridoma cells are screened to identify clones which produce an antibody whose ability to bind to the connective tissue growth factor-3 protein-specific antibody can be blocked by the connective tissue growth factor-3 protein antigen. Such antibodies comprise anti-idiotypic antibodies to the connective tissue growth factor-3 protein-specific antibody and can be used to immunize an animal to induce formation of further connective tissue growth factor-3 protein-specific antibodies.

It will be appreciated that Fab and F(ab')$_2$ and other fragments of the antibodies of the present invention may be used according to the methods disclosed herein. Such fragments are typically produced by proteolytic cleavage, using enzymes such as papain (to produce Fab fragments) or pepsin (to produce F(ab')$_2$ fragments). Alternatively, connective tissue growth factor-3 protein-binding fragments can be produced through the application of recombinant DNA technology or through synthetic chemistry.

Where in vivo imaging is used to detect enhanced levels of connective tissue growth factor-3 protein for tumor diagnosis in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. See, for review, Morrison, *Science* 229:1202 (1985); Oi et al., *BioTechniques* 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643 (1984); Neuberger et al., *Nature* 314:268 (1985).

Further suitable labels for the connective tissue growth factor-3 protein-specific antibodies of the present invention are provided below. Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include $^3$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At $^{212}$Pb, $^{47}$Sc, $^{109}$Pd, etc. $^{111}$In is a preferred isotope where in vivo imaging is used since it avoids the problem of dehalogenation of the $^{125}$I or $^{131}$I-labeled monoclonal antibody by the liver. In addition, this radionucleotide has a more favorable gamma emission energy for imaging (Perkins et al., *Eur. J. Nucl. Med.* 10:296-301 (1985); Carasquillo et al., *J. Nucl. Med.* 28:281-287 (1987)). For example, $^{111}$In coupled to monoclonal antibodies with 1-(P-isothiocyanatobenzyl)-DPTA has shown little uptake in non-tumorous tissues, particularly the liver, and therefore enhances specificity of tumor localization (Esteban et al., *J. Nucl. Med.* 28:861-870 (1987)).

Examples of suitable non-radioactive isotopic labels include $^{157}$Gd, $^{55}$Mn, $^{162}$Dy, $^{52}$Tr, and $^{56}$Fe. Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, and a fluorescamine label.

Examples of suitable toxin labels include diphtheria toxin, ricin, and cholera toxin.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and iron.

Typical techniques for binding the above-described labels to antibodies are provided by Kennedy et al., *Clin. Chim. Acta* 70:1-31 (1976), and Schurs et al., *Clin. Chim. Acta* 81:1-40 (1977). Coupling techniques mentioned in the latter are the glutaraldehyde method, the periodate method, the dimaleimide method, the m-maleimidobenzoyl-N-hydroxy-succinimide ester method, all of which methods are incorporated by reference herein.

Therapeutics: Connective Tissue Growth Factor-3 Protein

It will be appreciated by those skilled in the art that individuals with conditions characterized by a decrease in the standard or normal level of connective tissue growth factor-3 activity, can be treated by administration of connective tissue growth factor-3 protein. For example, it is believed that individuals in need of wound healing, tissue repair, or increased bone mass (i.e., patients with osteoporosis) would benefit from such treatment. Thus, the invention further provides a method of treating an individual in need of an increased level of connective tissue growth factor-3 activity comprising administering to such an individual a pharmaceutical composition comprising an effective amount of an isolated connective tissue growth factor-3 polypeptide of the invention, particularly a mature form of the connective tissue growth factor-3, effective to increase the connective tissue growth factor-3 activity level in such an individual.

The connective tissue growth factor-3 polypeptide composition will be formulated and dosed in a fashion consistent with good medical practice, taking into account the clinical condition of the individual patient (especially the side effects of treatment with connective tissue growth factor-3 polypeptide alone), the site of delivery of the connective tissue growth factor-3 polypeptide composition, the method of administration, the scheduling of administration, and other factors known to practitioners. The "effective amount" of connective tissue growth factor-3 polypeptide for purposes herein is thus determined by such considerations.

As a general proposition, the total pharmaceutically effective amount of connective tissue growth factor-3 polypeptide administered parenterally per dose will be in the range of about 1 µg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the connective tissue growth factor-3 polypeptide is typically administered at a dose rate of about 1 µg/kg/hour to about 50 µg/kg/hour, either by 1-4 injections per day or by continuous subcutaneous infusions, for example, using a mini-pump. An intravenous bag solution may also be employed. The key factor in selecting an appropriate dose is the result obtained, as measured by increases in antibody production, increases in splenocyte or thymocyte number, increase in splenic B-cells, etc. The length of treatment needed to observe changes and the interval following treatment for responses to occur appears to vary depending on the desired effect.

Pharmaceutical compositions containing the connective tissue growth factor-3 of the invention may be administered orally, rectally, parenterally, intracistemally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The connective tissue growth factor-3 polypeptide is also suitably administered by sustained-release systems. Suitable examples of sustained-release compositions include semi-permeable polymer matrices in the form of shaped articles, e.g., films, or microcapsules. Sustained-release matrices include polylactides (U.S. Pat. No. 3,773,919; EP 58,481), copolymers of L-glutamic acid and gamma-ethyl-L-glutamate (Sidman, U. et al., *Biopolymers* 22:547-556 (1983)), poly(2-hydroxyethyl methacrylate) (R. Langer et al., *J. Biomed. Mater. Res.* 15:167-277 (1981), and R. Langer, *Chem. Tech.* 12:98-105 (1982)), ethylene vinyl acetate (R. Langer et al., Id.) or poly-D-(−)-3-hydroxybutyric acid (EP 133,988). Sustained-release connective tissue growth factor-3 polypeptide compositions also include liposomally entrapped connective tissue growth factor-3 polypeptide. Liposomes containing connective tissue growth factor-3 polypeptide are prepared by methods known per se: DE 3,218,121; Epstein et al., *Proc. Natl. Acad. Sci. (USA)* 82:3688-3692 (1985); Hwang et al., *Proc. Natl. Acad. Sci. (USA)* 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal connective tissue growth factor-3 polypeptide therapy.

For parenteral administration, in one embodiment, the connective tissue growth factor-3 polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the connective tissue growth factor-3 polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

The connective tissue growth factor-3 polypeptide is typically formulated in such vehicles at a concentration of about 0.1 mg/ml to 100 mg/ml, preferably 1-10 mg/ml, at a pH of about 3 to 8. It will be understood that the use of certain of the foregoing excipients, carriers, or stabilizers will result in the formation of connective tissue growth factor-3 polypeptide salts.

Connective tissue growth factor-3 polypeptide to be used for therapeutic administration must be sterile. Sterility is readily accomplished by filtration through sterile filtration membranes (e.g., 0.2 micron membranes). Therapeutic connective tissue growth factor-3 polypeptide compositions generally are placed into a container having a sterile access port, for example, an intravenous solution bag or vial having a stopper pierceable by a hypodermic injection needle.

Connective tissue growth factor-3 polypeptide ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous connective tissue growth factor-3 polypeptide solution, and the resulting mixture is lyophilized. The infusion solution is prepared by reconstituting the lyophilized connective tissue growth factor-3 polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Therapeutics: Antibodies to Connective Tissue Growth Factor-3 Protein

The present invention is further directed to antibody-based therapies, which involve administering a connective tissue growth factor-3 antibody to a mammalian patient for treating disorders characterized by an overgrowth of connective tissue cells and most likely an over-expression of CTGF-3. Such disorders include cancer, arthritis, atherosclerosis, fibrositis (muscles, joints), fibrosis of vital organs, such as the liver and kidney, or fibrotic conditions (e.g., scleroderma, keloids). Methods for producing anti-connective tissue growth factor-3 polyclonal and monoclonal antibodies are described in detail above. Such antibodies may be provided in pharmaceutically acceptable compositions as known in the art or as described herein.

A summary of the ways in which the antibodies of the present invention may be used therapeutically includes binding connective tissue growth factor-3 locally or systemically in the body or by direct cytotoxicity of the antibody, e.g., as mediated by complement (CDC) or by effector cells (ADCC). Some of these approaches are described in more detail below. Armed with the teachings provided herein, one of ordinary skill in the art will know how to use the antibodies of the present invention for diagnostic, monitoring, or therapeutic purposes without undue experimentation.

The CTGF-3 antibody of the present invention may be administered by any means that achieve their intended purpose. Amounts and regimens for the administration of antibodies, their fragments or derivatives can be determined readily by those with ordinary skill in the clinical art of treating connective-tissue-related diseases.

For example, administration may be by parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

Compositions within the scope of this invention include all compositions wherein the antibody, fragment or derivative is contained in an amount effective to achieve its intended purpose. While individual needs vary, determination of optimal ranges of effective amounts of each component is within the skill of the art. The effective dose is a function of the individual chimeric or monoclonal antibody, the presence and nature of a conjugated therapeutic agent (see below), the patient and his clinical status, and can vary from about 10 µg/kg body weight to about 5000 mg/kg body weight. The preferred dosages comprise 0.1 to 500 mg/kg body wt. The composition may contain suitable pharmaceutically acceptable carriers comprising excipients and auxiliaries which facilitate processing of the active compounds into preparations which can be used pharmaceutically. Preferably, the preparations, contain from about 0.01 to 99 percent, preferably from about 20 to 75 percent of active compound(s), together with the excipient.

Similarly, preparations of a connective tissue growth factor-3 antibody or fragment of the present invention for parenteral administration, such as in detectably labeled form for imaging or in a free or conjugated form for therapy, include sterile aqueous or non-aqueous solutions, suspensions, and emulsions. Examples of non-aqueous solvents are propylene glycol, polyethylene glycol, vegetable oil such as olive oil, and injectable organic esters such as ethyl oleate. Aqueous carriers include water, alcoholic/aqueous solutions, emulsions or suspensions, including saline and buffered media, parenteral vehicles including sodium chloride solution, Ringer's dextrose, dextrose and sodium chloride, lactated Ringer's, or fixed oils. Intravenous vehicles include fluid and nutrient replenishers, such as those based on Ringer's dextrose, and the like. Preservatives and other additives may also be present, such as, for example, antimicrobials, anti-oxidants, chelating agents, and inert gases and the like. See, generally, *Remington's Pharmaceutical Science*, 16th ed., Mack Publishing Co., Easton, Pa., 1980.

In particular, the antibodies, fragments and derivatives of the present invention are useful for treating a subject having or developing connective tissue related disorders, as described herein, which are characterized by uncontrolled tissue growth. Such treatment comprises parenterally administering a single or multiple doses of the antibody, fragment or derivative, or a conjugate thereof.

The antibodies of this invention may be advantageously utilized in combination with other monoclonal or chimeric antibodies, or with lymphokines or hemopoietic growth factors, etc., which serve to increase the number or activity of effector cells which interact with the antibodies.

Preferred for human therapeutic use are high affinity murine and murine/human or human/human chimeric antibodies, and fragments, regions and derivatives having in vivo CTGF-3-inhibiting and/or neutralizing activity.

Chromosome Assays

The nucleic acid molecules of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marling chromosomal location. The mapping of DNAs to chromosomes according to the present invention is an important first step in correlating those sequences with genes associated with disease.

In certain preferred embodiments in this regard, the cDNA herein disclosed is used to clone genomic DNA of a connective tissue growth factor-3 protein gene. This can be accomplished using a variety of well known techniques and libraries, which generally are available commercially. The genomic DNA then is used for in situ chromosome mapping using well known techniques for this purpose. Typically, in accordance with routine procedures for chromosome mapping, some trial and error may be necessary to identify a genomic probe that gives a good in situ hybridization signal.

In addition, in some cases, sequences can be mapped to chromosomes by preparing PCR primers (preferably 15-25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified portion.

PCR mapping of somatic cell hybrids is a rapid procedure for assigning a particular DNA to a particular chromosome. Using the present invention with the same oligonucleotide primers, sublocalization can be achieved with panels of portions from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., *Human Chromosomes: A Manual Of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance In Man*, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Having generally described the invention, the same will be more readily understood by reference to the following examples, which are provided by way of illustration and are not intended as limiting.

EXAMPLES

Example 1

**Expression and Purification of Connective Tissue Growth Factor-3 in *E. coli***

The bacterial expression vector pQE9 (pD10) is used for bacterial expression in this example. (QIAGEN, Inc., 9259 Eton Avenue, Chatsworth, Calif., 91311). pQE9 encodes ampicillin antibiotic resistance ("Amp") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that an inserted DNA fragment encoding a polypeptide expresses that polypeptide with the six His residues (i.e., a "6×His tag")) covalently linked to the amino terminus of that polypeptide.

The DNA sequence encoding the desired portion of the connective tissue growth factor-3 protein lacking the hydrophobic leader sequence is amplified from the deposited cDNA clone using PCR oligonucleotide primers which anneal to the amino terminal sequences of the desired portion of the connective tissue growth factor-3 protein and to sequences in the deposited construct 3' to the cDNA coding sequence. Additional nucleotides containing restriction sites to facilitate cloning in the pQE9 vector are added to the 5' and 3' primer sequences, respectively.

For cloning the mature protein, the 5' primer has the sequence 5' CACCAC GGATCCAAGGTGCGTACCCAGCTGTGCCCG 3' (SEQ ID NO:4) containing the underlined BamH1 restriction site, which encodes 24 nucleotides of the connective tissue growth factor-3 protein coding sequence in FIG. 1 (SEQ ID NO:1) beginning immediately after the signal peptide. One of ordinary skill in the art would appreciate, of course, that the point in the protein coding sequence where the 5' primer begins may be varied to amplify a DNA segment encoding any desired portion of the complete connective tissue growth factor-3 protein shorter or longer than the mature form.

The 3' primer has the sequence 5' GATGT AAGCTTCGTGTCCCCATTCCCAGCCCG 3' (SEQ ID NO:5) containing the underlined HindIII restriction site followed by 21 nucleotides complementary to the sequence immediately downstream from the connective tissue growth factor-3 protein coding sequence in FIG. 1.

The amplified connective tissue growth factor-3 DNA fragment and the vector pQE9 are digested with BamHI and HindIII and the digested DNAs are then ligated together. Insertion of the connective tissue growth factor-3 DNA into the restricted pQE9 vector places the connective tissue growth factor-3 protein coding region downstream from the IPTG-inducible promoter and in-frame with an initiating AUG and the six histidine codons.

The ligation mixture is transformed into competent *E. coli* cells using standard procedures, such as those described in Sambrook et al., *Molecular Cloning: a Laboratory Manual*, 2nd Ed.; Cold Spring Harbor Laboratory Press, Cold Spring Harbor, N.Y. (1989). *E. coli* strain M15/rep4, containing multiple copies of the plasmid pREP4, which expresses lac repressor and confers kanamycin resistance ("Kan<sup>r</sup>"), is used in carrying out the illustrative example described herein. This strain, which is only one of many that are suitable for expressing connective tissue growth factor-3 protein, is available commercially from QIAGEN, Inc., supra. Transformants are identified by their ability to grow on LB plates in the presence of ampicillin and kanamycin. Plasmid DNA is isolated from resistant colonies and the identity of the cloned DNA confirmed by restriction analysis, PCR, and DNA sequencing.

Clones containing the desired constructs are grown overnight ("O/N") in liquid culture in LB media supplemented with both ampicillin (100 µg/ml) and kanamycin (25 µg/ml). The O/N culture is used to inoculate a large culture, at a dilution of approximately 1:100 to 1:250. The cells are grown to an optical density at 600 nm ("OD600") of between 0.4 and 0.6. Isopropyl-b-D-thiogalactopyranoside ("IPTG") is then added to a final concentration of 1 mM to induce transcription from lac repressor sensitive promoters, by inactivating the lacI repressor. Cells subsequently are incubated further for 3 to 4 hours. Cells are then harvested by centrifugation.

The cells are then stirred for 3-4 hours at 4° C. in 6M guanidine-HC1, pH8. The cell debris is removed by centrifugation, and the supernatant containing the connective tissue growth factor-3 is loaded onto a nickel-nitrilo-tri-acetic acid ("NiNTA") affinity resin column (available from QIAGEN, Inc., supra). Proteins with a 6×His tag bind to the NI-NTA resin with high affinity and can be purified in a simple one-step procedure (for details see: The QIAexpressionist, 1995, QIAGEN, Inc., supra). Briefly the supernatant is loaded onto the column in 6 M guanidine-HC1, pH8, the column is first washed with 10 volumes of 6 M guanidine-HC1, pH8, then washed with 10 volumes of 6 M guanidine-HC1 pH6, and finally the connective tissue growth factor-3 is eluted with 6 M guanidine-HC1, pH5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6 M-1 M urea gradient in 500 mM NaCl, 20% glycerol, 20 mM Tris/HC1 pH7.4, containing protease inhibitors. The renaturation should be performed over a period of 1.5 hours or more. After renaturation, the proteins can be eluted by the addition of 250 mM imidazole. Imidazole is removed by a final dialyzing step against PBS or 50 mM sodium acetate pH6 buffer plus 200 mM NaCl. The purified protein is stored at 4° C. or frozen at −80° C.

Example 2

Cloning and Expression of Connective Tissue Growth Factor-3 Protein in a Baculovirus Expression System

In this illustrative example, the plasmid shuttle vector pA2 is used to insert the cloned DNA encoding the complete protein, including its naturally associated secretary signal (leader) sequence, into a baculovirus to express the mature connective tissue growth factor-3 protein, using standard methods as described in Summers et al., *A Manual of Methods for Baculovirus Vectors and Insect Cell Culture Procedures*, Texas Agricultural Experimental Station Bulletin No. 1555 (1987). This expression vector contains the strong polyhedrin promoter of the *Autographa californica* nuclear polyhedrosis virus (AcMNPV) followed by convenient restriction sites such as BamHI and Asp718. The polyadenylation site of the simian virus 40 ("SV40") is used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate viable virus that express the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31-39 (1989).

The cDNA sequence encoding the full length connective tissue growth factor-3 protein in the deposited clone, including the AUG initiation codon and the naturally associated leader sequence shown in FIG. 1 (SEQ ID NO:2), is amplified using PCR oligonucleotide primers corresponding to the 5' and 3' sequences of the gene.

The 5' primer has the sequence 5' CGGCA GGATCCGCCATCATGAGAGGCACACCGAAGACCC 3' (SEQ ID NO:6) containing the underlined BamHI restriction enzyme site, an efficient signal for initiation of translation in eukaryotic cells, as described by Kozak, M., *J. Mol. Biol.* 196:947-950 (1987), followed by 22 bases of the sequence of the complete connective tissue growth factor-3 protein shown in FIG. 1, beginning with the AUG initiation codon.

The 3' primer has the sequence 5' GATGT GGTACCCGTGTCCCCATTCCCAGCCCG 3' (SEQ ID NO:7) containing the underlined Asp718 restriction site followed by 21 nucleotides complementary to the 3' noncoding sequence in FIG. 1.

The amplified fragment is isolated from a 1% agarose gel using a commercially available kit ("Geneclean," BIO 101 Inc., La Jolla, Calif.). The fragment is then digested with BamHI and Asp718, and again purified on a 1% agarose gel. This fragment is designated herein "F1."

The plasmid is digested with the restriction enzymes BamHI and Asp718 and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V1."

Fragment F1 and the dephosphorylated plasmid V1 are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria are identified that contain the plasmid with the human connective tissue growth factor-3 gene using the PCR method, in which one of the primers that is used to amplify the gene and the second primer is from well within the vector so that only those bacterial colonies containing the connective tissue growth factor-3 gene fragment will show amplification of the DNA. The sequence of the cloned fragment is confirmed by DNA sequencing. This plasmid is designated herein pBacconnective tissue growth factor-3.

Five μg of the plasmid pBacconnective tissue growth factor-3 is co-transfected with 1.0 μg of a commercially available linearized baculovirus DNA ("BACULOGOLD™ baculovirus DNA", Pharmingen, San Diego, Calif.), using the lipofection method described by Felgner et al., *Proc. Natl. Acad. Sci. USA* 84:7413-7417 (1987). One μg of BACULOGOLD™ virus DNA and 5 gg of the plasmid pBacconnective tissue growth factor-3 are mixed in a sterile well of a microtiter plate containing 50 μl of serum-free Grace's medium (Life Technologies Inc., Gaithersburg, Md.). Afterwards, 10 μl Lipofectin plus 90 μl Grace's medium are added, mixed and incubated for 15 minutes at room temperature. Then the transfection mixture is added drop-wise to Sf9 insect cells (ATCC™ CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation is continued at 27° C. for four days.

After four days, the supernatant is collected and a plaque assay is performed, as described by Summers and Smith, supra. An agarose gel with "Blue Gal" (Life Technologies Inc., Gaithersburg, Md.) is used to allow easy identification and isolation of gal-expressing clones, which produce bluestained plaques. (A detailed description of a "plaque assay" of this type can also be found in the user's guide for insect cell culture and baculovirology distributed by Life Technologies Inc., Gaithersburg, Md., pages 9-10). After appropriate incubation, blue stained plaques are picked with the tip of a micropipettor (e.g., Eppendorf). The agar containing the recombinant viruses is then resuspended in a microcentrifuge tube containing 200 μl of Grace's medium and the suspension containing the recombinant baculovirus is used to infect Sf9 cells seeded in 35 mm dishes. Four days later the supernatants of these culture dishes are harvested and then they are stored at 4° C. The recombinant virus is called V-connective tissue growth factor-3.

To verify the expression of the connective tissue growth factor-3 gene, Sf9 cells are grown in Grace's medium supplemented with 10% heat inactivated FBS. The cells are infected with the recombinant baculovirus V-connective tissue growth factor-3 at a multiplicity of infection ("MOI") of about 2. Six hours later the medium is removed and is replaced with SF900 II medium minus methionine and cysteine (available from Life Technologies Inc., Gaithersburg, Md.). If radiolabeled proteins are desired, 42 hours later, 5 μCi of $^{35}$S-methionine and 5 μCi $^{35}$S-cysteine (available from Amersham) are added. The cells are further incubated for 16 hours and then they are harvested by centrifugation. The proteins in the supernatant as well as the intracellular proteins are analyzed by SDS-PAGE followed by autoradiography (if radiolabeled). Microsequencing of the amino acid sequence of the amino terminus of purified protein may be used to determine the amino terminal sequence of the mature protein and thus the cleavage point and length of the secretory signal peptide.

Example 3

Cloning and Expression of Connective Tissue Growth Factor-3 in Mammalian Cells

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences, and intervening sequences flanked by donor and acceptor sites for RNA splicing. Highly efficient transcription can be achieved with the early and late promoters from SV40, the long terminal repeats (LTRs) from Retroviruses, e.g., RSV, HTLVI, HIVI, and the early promoter of the cytomegalovirus (CMV). However, cellular elements can also be used (e.g., human actin promoter). Suitable expression vectors for use in practicing the present invention include, for example, vectors such as pSVL and pMSG (Pharmacia, Uppsala, Sweden), pRSVcat (ATCC™ 37152), pSV2dhfr (ATCC™ 37146) and pBC12MI (ATCC™ 67109). Mammalian host cells that could be used include, human HeLa 293, H9 and Jurkat cells, mouse NIH3T3 and C127 cells, Cos 1, Cos 7 and CV1, quail QC1-3 cells, mouse L cells, and Chinese hamster ovary (CHO) cells.

Alternatively, the gene can be expressed in stable cell lines that contain the gene integrated into a chromosome. The co-transfection with a selectable marker such as dhfr, gpt, neomycin, or hygromycin allows the identification and isolation of the transfected cells.

The transfected gene can also be amplified to express large amounts of the encoded protein. Dihydrofolate reductase (DHFR) is a useful marker to develop cell lines that carry several hundred or even several thousand copies of the gene of interest. Another useful selection marker is the enzyme glutamine synthase (GS) (Murphy et al., *Biochem J,* 227:277-279 (1991); Bebbington et al., *Bio/Technology* 10:169-175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

The expression vectors pC1 and pC4 contain the strong promoter (LTR) of the Rous Sarcoma Virus (Cullen et al., *Molecular and Cellular Biology,* 438-447 (March 1985)) plus a fragment of the CMV-enhancer (Boshart et al., *Cell* 41:521-530 (1985)). Multiple cloning sites, e.g., with the restriction enzyme cleavage sites BamHI, XbaI, and Asp718, facilitate the cloning of the gene of interest. In addition, vectors contain the 3' intron and the polyadenylation and termination signal of the rat preproinsulin gene.

Example 3(a)

Cloning and Expression in COS Cells

The expression plasmid, pCTGF-3 HA, is made by cloning a cDNA encoding connective tissue growth factor-3 into the expression vector pcDNAI/Amp or pcDNAIII (which can be obtained from Invitrogen, Inc.).

The expression vector pcDNAI/amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson et al., *Cell* 37:767 (1984). The fusion of the HA tag to the target protein allows easy detection and recovery of the recombinant protein with an antibody that recognizes the HA epitope. pcDNAIII contains, in addition, the selectable neomycin marker.

A DNA fragment encoding the connective tissue growth factor-3 protein is cloned into the polylinker region of the vector so that recombinant protein expression is directed by the CMV promoter. The plasmid construction strategy is as follows. The connective tissue growth factor-3 cDNA of the deposited clone is amplified using primers that contain convenient restriction sites, much as described above for construction of vectors for expression of connective tissue growth factor-3 in *E. coli*. Suitable primers include the following, which are used in this example.

The 5' primer, containing the underlined BamHI site, a Kozak sequence, an AUG start codon, and 7 codons of the 5' coding region of the complete connective tissue growth factor-3 has the following sequence:

(SEQ ID NO: 8)
5' GCTCGGATCCGCCATCATGAGAGGCACACCGAAGACCCAC 3'.

The 3' primer, containing the underlined XbaI site, a stop codon, and 32 bp of 3' coding sequence has the following sequence (at the 3' end):

(SEQ ID NO: 9)
5' GATGTTCTAGAAGAAGGCACTGTTTTGTGGACTGCGACCCCTG 3'.

The PCR amplified DNA fragment and the vector, pcDNAI/Amp, are digested with BamHI and XbaI and then ligated. The ligation mixture is transformed into *E. coli* strain SURE (available from Stratagene Cloning Systems, 11099 North Torrey Pines Road, La Jolla, Calif. 92037). The transformed culture is then plated on ampicillin media plates that are then incubated to allow growth of ampicillin resistant colonies. Plasmid DNA is isolated from resistant colonies and examined by restriction analysis or other means for the presence of the connective tissue growth factor-3-encoding fragment.

For expression of recombinant connective tissue growth factor-3, COS cells are transfected with an expression vector, as described above, using DEAE-DEXTRAN, as described, for instance, in Sambrook et al., *Molecular Cloning: a Laboratory Manual,* Cold Spring Laboratory Press, Cold Spring Harbor, N.Y. (1989). Cells are incubated under conditions for expression of connective tissue growth factor-3 by the vector.

Expression of the connective tissue growth factor-3 HA fusion protein is detected by radiolabeling and immunoprecipitation, using methods described in, for example Harlow et al., *Antibodies: a Laboratory Manual,* 2nd Ed.; Cold Spring Harbor Laboratory Press, Cold Spring Harbor, N.Y. (1988). To this end, two days after transfection, the cells are labeled by incubation for 8 hours in media containing $^{35}$S-cysteine. The cells and the media are collected, and the cells washed and then lysed with detergent-containing RIPA buffer: 150 mM NaCl, 1% NP-40, 0.1% SDS, 1% NP-40, 0.5% DOC, 50 mM TRIS, pH 7.5, as described by Wilson et al. cited above. Proteins are precipitated from the cell lysate and from the culture media using an HA-specific monoclonal antibody. The precipitated proteins are then analyzed by SDS-PAGE gels and autoradiography. An expression product of the expected size is seen in the cell lysate, which is not seen in negative controls.

Example 3(b)

Cloning and Expression in CHO Cells

The vector pC4 is used for the expression of connective tissue growth factor-3 protein. Plasmid pC4 is a derivative of the plasmid pSV2-dhfr [ATCC™ Accession No. 37146]. The plasmid contains the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate (MTX). The amplification of the DHFR genes in cells resistant to methotrexate has been well documented (see, e.g., Alt, F. W., et al., *J. Biol. Chem.* 253:1357-1370 (1978); Hamlin, J. L. and Ma, C., *Biochem. et Biophys. Acta* 1097:107-143 (1990); Page, M. J. and Sydenham, M. A., *Biotechnology* 9:64-68 (1991)). Cells grown in increasing concentrations of MTX develop resistance to the drug by overproducing the target enzyme, DHFR, as a result of amplification of the DHFR gene. If a second gene is linked to the DHFR gene it is usually co-amplified and over-expressed. It is known in the art that this approach may be used to develop cell lines carrying more than 1,000 copies of the amplified gene(s). Subsequently, when the methotrexate is withdrawn, cell lines are obtained that contain the amplified gene integrated into one or more chromosome(s) of the host cell.

For expressing the gene of interest, plasmid pC4 contains the strong promoter of the long terminal repeat (LTR) of the Rous Sarcoma Virus (Cullen et al., *Molecular and Cellular Biology* 5:438-447 (March 1985)), plus a fragment isolated from the enhancer of the immediate early gene of human cytomegalovirus (CMV) (Boshart et al., *Cell* 41:521-530 (1985)). Downstream from the promoter are restriction enzyme cleavage sites that allow integration of the genes. Behind these cloning sites, the plasmid contains the 3' intron and polyadenylation site of the rat preproinsulin gene. Other high efficiency promoters can also be used for the expression, e.g., the human (β-actin promoter, the SV40 early or late promoters or the long terminal repeats from other retroviruses, e.g., HIV and HTLVI. Clontech's Tet-Off and Tet-On gene expression systems and similar systems can be used to express the connective tissue growth factor-3 in a regulated way in mammalian cells (Gossen, M., & Bujard, H., *Proc. Natl. Acad. Sci. USA* 89: 5547-5551 (1992)). For the polyadenylation of the mRNA, other signals, e.g., from the human growth hormone or globin genes can be used as well. Stable cell lines carrying a gene of interest integrated into the chromosomes can also be selected upon co-transfection with a selectable marker such as gpt, G418, or hygromycin. It is advantageous to use more than one selectable marker in the beginning, e.g., G418 plus methotrexate.

The plasmid pC4 is digested with the restriction enzymes BamHI and Asp718, and then dephosphorylated using calf intestinal phosphates by procedures known in the art. The vector is then isolated from a 1% agarose gel.

The DNA sequence encoding the complete connective tissue growth factor-3 protein including its leader sequence is amplified using PCR oligonucleotide primers corresponding to the 5' and 3' sequences of the gene.

The 5' primer has the sequence 5' CGGCA GGATCCGCCATCATGAGAGGCACACCGAAGACCC 3' (SEQ ID NO:6) containing the underlined BamH1 restriction enzyme site followed by an efficient signal for initiation of translation in eukaryotes, as described by Kozak, M., *J. Mol. Biol.* 196:947-950 (1987), and 22 bases of the coding sequence of connective tissue growth factor-3 shown in FIG. 1 (SEQ ID NO:1).

The 3' primer has the sequence 5' GATGT GGTACCCGTGTCCCCATTCCCAGCCCG 3' (SEQ ID NO:7) containing the underlined Asp718 restriction site followed by 21 nucleotides complementary to the non-translated region of the connective tissue growth factor-3 gene shown in FIG. 1 (SEQ ID NO:1).

The amplified fragment is digested with the endonucleases BamHI and Asp718, and then purified again on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. Five μg of the expression plasmid pC4 is cotransfected with 0.5 μg of the plasmid pSV2-neo using lipofectin (Felgner et al., supra). The plasmid pSV2-neo contains a dominant selectable marker, the neo gene from Tn5, encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10-14 days, single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 mM, 20 mM). The same procedure is repeated until clones are obtained which grow at a concentration of 100-200 μM. Expression of the desired gene product is analyzed, for instance, by SDS-PAGE and Western blot or by reverse phase HPLC analysis.

Example 4

Tissue Distribution of Connective Tissue Growth Factor-3 Protein Expression

Northern blot analysis was carried out to examine connective tissue growth factor-3 gene expression in human tissues, using methods described by, among others, Sambrook et al., cited above. A cDNA probe containing the entire nucleotide sequence of the connective tissue growth factor-3 protein (SEQ ID NO:1) was labeled with $^{32P}$ using the REDIPRIME™ DNA labeling system (Amersham Life Science), according to manufacturer's instructions. After labelling, the probe was purified using a CHROMA SPIN-100™ column (Clontech Laboratories, Inc.), according to manufacturer's protocol number PT1200-1. The purified labelled probe was then used to examine various human tissues for connective tissue growth factor-3 mRNA.

Multiple Tissue Northern (MTN) blots containing various human tissues (H) were obtained from Clontech and were examined with labelled probe using EXPRESSHYB™ hybridization solution (Clontech) according to manufacturer's protocol number PT 1190-1. Following hybridization and washing, the blots were mounted and exposed to film at −70° C. overnight, and films developed according to standard procedures.

By Northern expression analysis, CTGF-3 was abundantly expressed in ovary and Hela cells, as well as other organs, as shown in the Table below.

| | |
|---|---|
| heart | ++ |
| lung | + |
| skeletal muscle | ++ |
| adrenal medulla | ++ |
| adrenal cortex | +++ |
| Hela cells | ++++++++ |
| thymus | ++ |
| prostate | +++ |
| ovary | +++++++ |
| small intestine | + |
| colon | +++ |

It is expected that fibrotic skin or liver would also express high levels of CTGF-3.

It will be clear that the invention may be practiced otherwise than as particularly described in the foregoing description and examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

What is claimed is:

1. An isolated antibody or fragment thereof that specifically binds to a protein selected from the group consisting of:
   (a) a protein whose amino acid sequence consists of amino acid residues −18 to 231 of SEQ ID NO:2;
   (b) a protein whose amino acid sequence consists of amino acid residues 1 to 231 of SEQ ID NO:2;
   (c) a protein whose amino acid sequence consists of a portion of SEQ ID NO:2, wherein said portion is at least 30 contiguous amino acid residues in length; and
   (d) a protein whose amino acid sequence consists of a portion of SEQ ID NO:2, wherein said portion is at least 50 contiguous amino acid residues in length.

2. The antibody or fragment thereof of claim 1 that specifically binds protein (a).

3. The antibody or fragment thereof of claim 1 that specifically binds protein (b).

4. The antibody or fragment thereof of claim 1 that specifically binds protein (c).

5. The antibody or fragment thereof of claim 1 that specifically binds protein (d).

6. The antibody or fragment thereof of claim 2 that specifically binds protein (b).

7. The antibody or fragment thereof of claim 3 wherein said protein bound by said antibody or fragment thereof is glycosylated.

8. The antibody or fragment thereof of claim 3 wherein said antibody or fragment thereof is human.

9. The antibody or fragment thereof of claim 3 wherein said antibody or fragment thereof is polyclonal.

10. The antibody or fragment thereof of claim 3 wherein said antibody or fragment thereof is monoclonal.

11. The antibody or fragment thereof of claim 3 which is selected from the group consisting of:
    (a) a chimeric antibody or fragment thereof
    (b) a humanized antibody or fragment thereof
    (c) a single chain antibody; and
    (d) a Fab fragment.

12. The antibody or fragment thereof of claim 3 which is labeled.

13. The antibody or fragment thereof of claim 3 wherein said antibody or fragment thereof specifically binds to said protein in a Western blot or an ELISA.

14. An isolated cell that produces the antibody or fragment thereof of claim 3.

15. A method of detecting a protein in a biological sample comprising: (a) contacting the biological sample with the antibody or fragment thereof of claim 3; and (b) detecting a protein that is specifically bound by the antibody or fragment thereof of claim 3 in the biological sample.

16. An isolated antibody or fragment thereof that specifically binds a CTGF-3 protein purified from a cell culture wherein said CTGF-3 protein is encoded by a polynucleotide encoding amino acids 1 to 231 of SEQ ID NO:2.

17. The antibody or fragment thereof of claim 16 wherein said antibody or fragment thereof is monoclonal.

18. The antibody or fragment thereof of claim 16 wherein said antibody or fragment thereof is polyclonal.

19. The antibody or fragment thereof of claim 16 wherein said antibody or fragment thereof is human.

20. The antibody or fragment thereof of claim 16 which is selected from the group consisting of:
 (a) a chimeric antibody or fragment thereof
 (b) a humanized antibody or fragment thereof
 (c) a single chain antibody; and
 (d) a Fab fragment.

* * * * *

UNITED STATES PATENT AND TRADEMARK OFFICE
CERTIFICATE OF CORRECTION

PATENT NO. : 7,737,257 B2  
APPLICATION NO. : 11/962282  
DATED : June 15, 2010  
INVENTOR(S) : Ebner et al.

Page 1 of 1

It is certified that error appears in the above-identified patent and that said Letters Patent is hereby corrected as shown below:

In the Specification:

At Column 1, Line 20, delete "entitled "PF319C3_SeqList.txt" (14,109 bytes, created Dec. 20, 2007)," and insert therefor --entitled "PF319C3_SubSeqList.txt" (14,435 bytes, created October 27, 2008),--.

In the Claims:

At Column 48, Claim 11, Lines 63 and 64, delete "thereof" and insert therefor --thereof;--.  
At Column 50, Claim 20, Lines 11 and 12, delete "thereof" and insert therefor --thereof;--.

Signed and Sealed this

Fifth Day of October, 2010

David J. Kappos  
*Director of the United States Patent and Trademark Office*

SEQUENCE LISTING

<160> NUMBER OF SEQ ID NOS: 13

<210> SEQ ID NO 1
<211> LENGTH: 1285
<212> TYPE: DNA
<213> ORGANISM: Homo sapiens
<220> FEATURE:
<221> NAME/KEY: CDS
<222> LOCATION: (9)..(758)
<220> FEATURE:
<221> NAME/KEY: sig_peptide
<222> LOCATION: (9)..(65)
<220> FEATURE:
<221> NAME/KEY: mat_peptide
<222> LOCATION: (66)..()

<400> SEQUENCE: 1

```
cagggac atg aga ggc aca ccg aag acc cac ctc ctg gcc ttc tcc ctc      50
        Met Arg Gly Thr Pro Lys Thr His Leu Leu Ala Phe Ser Leu
            -15                 -10 ctc tgc ctc ctc tca aag gtg cgt acc cag ctg tgc ccg aca cca tgt      98
Leu Cys Leu Leu Ser Lys Val Arg Thr Gln Leu Cys Pro Thr Pro Cys
-5          -1  1               5                  10 acc tgc ccc tgg cca cct ccc cga tgc ccg ctg gga gta ccc ctg gtg     146
Thr Cys Pro Trp Pro Pro Pro Arg Cys Pro Leu Gly Val Pro Leu Val
            15                  20                  25 ctg gat ggc tgt ggc tgc tgc cgg gta tgt gca cgg cgg ctg ggg gag     194
Leu Asp Gly Cys Gly Cys Cys Arg Val Cys Ala Arg Arg Leu Gly Glu
                30                  35                  40 ccc tgc gac caa ctc cac gtc tgc gac gcc agc cag ggc ctg gtc tgc     242
Pro Cys Asp Gln Leu His Val Cys Asp Ala Ser Gln Gly Leu Val Cys
    45                  50                  55 cag ccc ggg gca gga ccc ggt ggc cgg ggg gcc ctg tgc ctc ttg gca     290
Gln Pro Gly Ala Gly Pro Gly Gly Arg Gly Ala Leu Cys Leu Leu Ala
60                  65                  70                  75 gag gac gac agc agc tgt gag gtg aac ggc cgc ctg tat cgg gaa ggg     338
Glu Asp Asp Ser Ser Cys Glu Val Asn Gly Arg Leu Tyr Arg Glu Gly
                80                  85                  90 gag acc ttc cag ccc cac tgc agc atc cgc tgc cgc tgc gag gac ggc     386
Glu Thr Phe Gln Pro His Cys Ser Ile Arg Cys Arg Cys Glu Asp Gly
            95                  100                 105 ggc ttc acc tgc gtg ccg ctg tgc agc gag gat gtg cgg ctg ccc agc     434
Gly Phe Thr Cys Val Pro Leu Cys Ser Glu Asp Val Arg Leu Pro Ser
        110                 115                 120 tgg gac tgc ccc cac ccc agg agg gtc gag gtc ctg ggc aag tgc tgc     482
Trp Asp Cys Pro His Pro Arg Arg Val Glu Val Leu Gly Lys Cys Cys
    125                 130                 135 cct gag tgg gtg tgc ggc caa gga ggg gga ctg ggg acc cag ccc ctt     530
Pro Glu Trp Val Cys Gly Gln Gly Gly Gly Leu Gly Thr Gln Pro Leu
140                 145                 150                 155 cca gcc caa gga ccc cag ttt tct ggc ctt gtc tct tcc ctg ccc cct     578
Pro Ala Gln Gly Pro Gln Phe Ser Gly Leu Val Ser Ser Leu Pro Pro
                160                 165                 170
```

```
ggt gtc ccc tgc cca gaa tgg agc acg gcc tgg gga ccc tgc tcg acc    626
Gly Val Pro Cys Pro Glu Trp Ser Thr Ala Trp Gly Pro Cys Ser Thr
        175                 180                 185 acc tgt ggg ctg ggc atg gcc acc cgg gtg tcc aac cag aac cgc ttc    674
Thr Cys Gly Leu Gly Met Ala Thr Arg Val Ser Asn Gln Asn Arg Phe
        190                 195                 200 tgc cga ctg gag acc cag cgc cgc ctg tgc ctg tcc agg ccc tgc cca    722
Cys Arg Leu Glu Thr Gln Arg Arg Leu Cys Leu Ser Arg Pro Cys Pro
    205                 210                 215 ccc tcc agg ggt cgc agt cca caa aac agt gcc ttc tagagccggg         768
Pro Ser Arg Gly Arg Ser Pro Gln Asn Ser Ala Phe
220                 225                 230 ctgggaatgg ggacacggtg tccaccatcc ccagctggtg gccctgtgcc tgggccctgg   828
gctgatggaa gatggtccgt gcccaggccc ttggctgcag caacacttt agcttgggtc    888 caccatgcag aacaccaata ttaacacgct gcctggtctg tctggatccc gaggtatggc   948
agaggtgcaa gacctagtcc cctttcctct aactcactgc ctaggaggct ggccaaggtg  1008
tccagggtcc tctagcccac tccctgccta cacacacagc ctatatcaaa catgcacacg  1068
ggcgagcttt ctctccgact tccctgggc aagagatggg acaagcagtc ccttaatatt  1128
gaggctgcag caggtgctgg gctggactgg ccatttttct gggggtagga tgaagagaag  1188
gcacacagag attctggatc tcctgctgcc ttttctggaa tttgtaaaat tgttcctgaa  1248
tacaagccta tgcgtgaaaa aaaaaaaaaa aaaaaaa                           1285

<210> SEQ ID NO 2
<211> LENGTH: 250
<212> TYPE: PRT
<213> ORGANISM: Homo sapiens

<400> SEQUENCE: 2

Met Arg Gly Thr Pro Lys Thr His Leu Leu Ala Phe Ser Leu Leu Cys
            -15                 -10                  -5

Leu Leu Ser Lys Val Arg Thr Gln Leu Cys Pro Thr Pro Cys Thr Cys
        -1   1               5                  10

Pro Trp Pro Pro Arg Cys Pro Leu Gly Val Pro Leu Val Leu Asp
        15                  20                  25

Gly Cys Gly Cys Cys Arg Val Cys Ala Arg Arg Leu Gly Glu Pro Cys
 30                  35                  40                  45

Asp Gln Leu His Val Cys Asp Ala Ser Gln Gly Leu Val Cys Gln Pro
                 50                  55                  60

Gly Ala Gly Pro Gly Gly Arg Gly Ala Leu Cys Leu Leu Ala Glu Asp
             65                  70                  75

Asp Ser Ser Cys Glu Val Asn Gly Arg Leu Tyr Arg Glu Gly Glu Thr
         80                  85                  90

Phe Gln Pro His Cys Ser Ile Arg Cys Arg Cys Glu Asp Gly Gly Phe
     95                 100                 105

Thr Cys Val Pro Leu Cys Ser Glu Asp Val Arg Leu Pro Ser Trp Asp
110                 115                 120                 125

Cys Pro His Pro Arg Arg Val Glu Val Leu Gly Lys Cys Cys Pro Glu
                130                 135                 140

Trp Val Cys Gly Gln Gly Gly Gly Leu Gly Thr Gln Pro Leu Pro Ala
            145                 150                 155

Gln Gly Pro Gln Phe Ser Gly Leu Val Ser Ser Leu Pro Pro Gly Val
        160                 165                 170
```

```
Pro Cys Pro Glu Trp Ser Thr Ala Trp Gly Pro Cys Ser Thr Thr Cys
    175                 180                 185

Gly Leu Gly Met Ala Thr Arg Val Ser Asn Gln Asn Arg Phe Cys Arg
190                 195                 200                 205

Leu Glu Thr Gln Arg Arg Leu Cys Leu Ser Arg Pro Cys Pro Pro Ser
                210                 215                 220

Arg Gly Arg Ser Pro Gln Asn Ser Ala Phe
            225                 230
```

<210> SEQ ID NO 3
<211> LENGTH: 349
<212> TYPE: PRT
<213> ORGANISM: Homo sapiens

<400> SEQUENCE: 3

```
Met Thr Ala Ala Ser Met Gly Pro Val Arg Val Ala Phe Val Val Leu
1               5                   10                  15

Leu Ala Leu Cys Ser Arg Pro Ala Val Gly Gln Asn Cys Ser Gly Pro
                20                  25                  30

Cys Arg Cys Pro Asp Glu Pro Ala Pro Arg Cys Pro Ala Gly Val Ser
            35                  40                  45

Leu Val Leu Asp Gly Cys Gly Cys Cys Arg Val Cys Ala Lys Gln Leu
50                  55                  60

Gly Glu Leu Cys Thr Glu Arg Asp Pro Cys Asp Pro His Lys Gly Leu
65                  70                  75                  80

Phe Cys Asp Phe Gly Ser Pro Ala Asn Arg Lys Ile Gly Val Cys Thr
                85                  90                  95

Ala Lys Asp Gly Ala Pro Cys Ile Phe Gly Gly Thr Val Tyr Arg Ser
            100                 105                 110

Gly Glu Ser Phe Gln Ser Ser Cys Lys Tyr Gln Cys Thr Cys Leu Asp
        115                 120                 125

Gly Ala Val Gly Cys Met Pro Leu Cys Ser Met Asp Val Arg Leu Pro
130                 135                 140

Ser Pro Asp Cys Pro Phe Pro Arg Arg Val Lys Leu Pro Gly Lys Cys
145                 150                 155                 160

Cys Glu Glu Trp Val Cys Asp Glu Pro Lys Asp Gln Thr Val Val Gly
                165                 170                 175

Pro Ala Leu Ala Ala Tyr Arg Leu Glu Asp Thr Phe Gly Pro Asp Pro
            180                 185                 190

Thr Met Ile Arg Ala Asn Cys Leu Val Gln Thr Thr Glu Trp Ser Ala
        195                 200                 205

Cys Ser Lys Thr Cys Gly Met Gly Ile Ser Thr Arg Val Thr Asn Asp
210                 215                 220

Asn Ala Ser Cys Arg Leu Glu Lys Gln Ser Arg Leu Cys Met Val Arg
225                 230                 235                 240

Pro Cys Glu Ala Asp Leu Glu Glu Asn Ile Lys Lys Gly Lys Lys Cys
                245                 250                 255

Ile Arg Thr Pro Lys Ile Ser Lys Pro Ile Lys Phe Glu Leu Ser Gly
            260                 265                 270

Cys Thr Ser Met Lys Thr Tyr Arg Ala Lys Phe Cys Gly Val Cys Thr
        275                 280                 285

Asp Gly Arg Cys Cys Thr Pro His Arg Thr Thr Thr Leu Pro Val Glu
290                 295                 300

Phe Lys Cys Pro Asp Gly Glu Val Met Lys Lys Asn Met Met Phe Ile
305                 310                 315                 320
```

Lys Thr Cys Ala Cys His Tyr Asn Cys Pro Gly Asp Asn Asp Ile Phe
            325                 330                 335

Glu Ser Leu Tyr Tyr Arg Lys Met Tyr Gly Asp Met Ala
            340                 345

<210> SEQ ID NO 4
<211> LENGTH: 36
<212> TYPE: DNA
<213> ORGANISM: Artificial Sequence
<220> FEATURE:
<223> OTHER INFORMATION: 5' primer with BamHI site

<400> SEQUENCE: 4
caccacggat ccaaggtgcg tacccagctg tgcccg                                 36

<210> SEQ ID NO 5
<211> LENGTH: 32
<212> TYPE: DNA
<213> ORGANISM: Artificial Sequence
<220> FEATURE:
<223> OTHER INFORMATION: 3' primer with HindIII site

<400> SEQUENCE: 5
gatgtaagct tcgtgtcccc attcccagcc cg                                     32

<210> SEQ ID NO 6
<211> LENGTH: 39
<212> TYPE: DNA
<213> ORGANISM: Artificial Sequence
<220> FEATURE:
<223> OTHER INFORMATION: 5' primer with BamHI site

<400> SEQUENCE: 6
cggcaggatc cgccatcatg agaggcacac cgaagaccc                              39

<210> SEQ ID NO 7
<211> LENGTH: 32
<212> TYPE: DNA
<213> ORGANISM: Artificial Sequence
<220> FEATURE:
<223> OTHER INFORMATION: 3' primer with Asp718 site

<400> SEQUENCE: 7
gatgtggtac ccgtgtcccc attcccagcc cg                                     32

<210> SEQ ID NO 8
<211> LENGTH: 40
<212> TYPE: DNA
<213> ORGANISM: Artificial Sequence
<220> FEATURE:
<223> OTHER INFORMATION: 5' primer with BamHI site

<400> SEQUENCE: 8
gctcggatcc gccatcatga gaggcacacc gaagacccac                             40

<210> SEQ ID NO 9
<211> LENGTH: 43
<212> TYPE: DNA
<213> ORGANISM: Artificial Sequence
<220> FEATURE:
<223> OTHER INFORMATION: 3' primer with XbaI site

<400> SEQUENCE: 9
gatgttctag aagaaggcac tgttttgtgg actgcgaccc ctg                         43

<210> SEQ ID NO 10
<211> LENGTH: 264
<212> TYPE: DNA
<213> ORGANISM: Homo Sapiens
<220> FEATURE:
<221> NAME/KEY: Unsure
<222> LOCATION: (56)..(56)
<223> OTHER INFORMATION: May be any nucleotide.
<220> FEATURE:
<221> NAME/KEY: Unsure
<222> LOCATION: (128)..(128)
<223> OTHER INFORMATION: May be any nucleotide.
<220> FEATURE:
<221> NAME/KEY: Unsure
<222> LOCATION: (246)..(246)
<223> OTHER INFORMATION: May be any nucleotide.

<400> SEQUENCE: 10

```
ctggtggccc tgtgcctggg ccctgggctg atggaagatg gtccgtgccc aggccnttgg      60
ctgcaggcaa cactttagct tgggtccacc atgcagaaca ccaatattaa cacgctgcct     120
ggtctgtntg datcccgagg tatggcagag gtgcaagacc tagtcctctt tcctctaact     180
cactgcctag gaggctggcc aaggtgtcca gggtcctcta gcccacttcc tgcctacaca     240
cacagnctat atcaaacatg caca                                            264
```

<210> SEQ ID NO 11
<211> LENGTH: 239
<212> TYPE: DNA
<213> ORGANISM: Homo Sapiens
<220> FEATURE:
<221> NAME/KEY: Unsure
<222> LOCATION: (5)..(5)
<223> OTHER INFORMATION: May be any nucleotide.
<220> FEATURE:
<221> NAME/KEY: Unsure
<222> LOCATION: (10)..(10)
<223> OTHER INFORMATION: May be any nucleotide.
<220> FEATURE:
<221> NAME/KEY: Unsure
<222> LOCATION: (85)..(85)
<223> OTHER INFORMATION: May be any nucleotide.
<220> FEATURE:
<221> NAME/KEY: Unsure
<222> LOCATION: (115)..(115)
<223> OTHER INFORMATION: May be any nucleotide.
<220> FEATURE:
<221> NAME/KEY: Unsure
<222> LOCATION: (165)..(165)
<223> OTHER INFORMATION: May be any nucleotide.
<220> FEATURE:
<221> NAME/KEY: Unsure
<222> LOCATION: (201)..(201)
<223> OTHER INFORMATION: May be any nucleotide.
<220> FEATURE:
<221> NAME/KEY: Unsure
<222> LOCATION: (219)..(219)
<223> OTHER INFORMATION: May be any nucleotide.
<220> FEATURE:
<221> NAME/KEY: Unsure
<222> LOCATION: (224)..(224)
<223> OTHER INFORMATION: May be any nucleotide.
<220> FEATURE:
<221> NAME/KEY: Unsure
<222> LOCATION: (236)..(236)
<223> OTHER INFORMATION: May be any nucleotide.

<400> SEQUENCE: 11

```
ggcanagggn cacaccgaag acccacctcc tggccttctc cctcctctgc ctcctctcaa      60
aggtgcgtac ccagctgtgc ccganaccat gtacctgccc ctgggcacct ccccnatgcc     120
cgctgggagt acccctggtg ctggatggct gtggctgctg ccggngttat gtgcacggcg     180
```

```
gctggggag ccctgcacta nactccacgt ctgcaaggnc agcnaagggc ctggtntgc      239
```

<210> SEQ ID NO 12
<211> LENGTH: 313
<212> TYPE: DNA
<213> ORGANISM: Homo Sapiens
<220> FEATURE:
<221> NAME/KEY: Unsure
<222> LOCATION: (23)..(23)
<223> OTHER INFORMATION: May be any nucleotide.
<220> FEATURE:
<221> NAME/KEY: Unsure
<222> LOCATION: (28)..(28)
<223> OTHER INFORMATION: May be any nucleotide.
<220> FEATURE:
<221> NAME/KEY: Unsure
<222> LOCATION: (265)..(265)
<223> OTHER INFORMATION: May be any nucleotide.

<400> SEQUENCE: 12

```
ccaatattaa cacgctgcct ggnctgtntg gttcccgagg tatggcagag gtgcaagacc     60
tagtcccctt tcctctaact cactgcctag gaggctggcc aaggtgtcca gggtcctcta    120
gcccactccc tgcctacaca cacagcctat atcaaacatg cacacgggcg agctttctct    180
ccgacttccc ctgggcaaga gatgggacaa gcagtccctt aatattgagg ctgcagcagg    240
tgctgggctg gactggccat ttttntgggg gtaggatgaa gagaaggcac acagagattc    300
tggatctcct gct                                                       313
```

<210> SEQ ID NO 13
<211> LENGTH: 60
<212> TYPE: DNA
<213> ORGANISM: Homo Sapiens
<220> FEATURE:
<221> NAME/KEY: Unsure
<222> LOCATION: (36)..(36)
<223> OTHER INFORMATION: May be any nucleotide.
<220> FEATURE:
<221> NAME/KEY: Unsure
<222> LOCATION: (38)..(38)
<223> OTHER INFORMATION: May be any nucleotide.

<400> SEQUENCE: 13

```
gatctcctgc tgcctttcct ggagtttgta aaattntncc tgaatacaag cctatgcgtg     60
```